(12) United States Patent
Brunicardi

(10) Patent No.: US 6,716,824 B1
(45) Date of Patent: Apr. 6, 2004

(54) TREATMENT OF PANCREATIC ADENOCARCINOMA BY CYTOTOXIC GENE THERAPY

(76) Inventor: F. Charles Brunicardi, 4036 Case St., Houston, TX (US) 77005

(*) Notice: Subject to any disclaimer, the term of this patent is extended or adjusted under 35 U.S.C. 154(b) by 0 days.

(21) Appl. No.: 09/686,631

(22) Filed: Oct. 11, 2000

Related U.S. Application Data

(60) Provisional application No. 60/161,109, filed on Oct. 22, 1999, and provisional application No. 60/224,382, filed on Aug. 9, 2000.

(51) Int. Cl.$^7$ .................. A61K 31/70; A01N 43/04; A01N 63/00; C12N 15/00; C12N 15/63
(52) U.S. Cl. ............. 514/44; 424/93.2; 435/320.1; 435/455
(58) Field of Search .................. 435/325, 320.1, 435/455; 424/93.21, 93.2; 514/44; 800/3, 8, 9, 11, 13

(56) References Cited

U.S. PATENT DOCUMENTS

| | | | |
|---|---|---|---|
| 5,631,236 A | 5/1997 | Woo et al. | 514/44 |
| 5,674,703 A | 10/1997 | Woo et al. | 435/69.1 |
| 5,723,333 A | 3/1998 | Levine et al. | 435/325 |
| 5,728,379 A | 3/1998 | Martuza et al. | 435/456 X |
| 5,747,325 A | 5/1998 | Newgard | 435/325 |
| 5,792,656 A | 8/1998 | Newgard | 435/6 X |
| 5,811,266 A | 9/1998 | Newgard | 435/69.4 |
| 5,837,283 A | 11/1998 | McDonald et al. | 424/450 |
| 5,837,693 A | 11/1998 | German et al. | 514/44 |
| 5,858,973 A | 1/1999 | Habener et al. | 514/12 |
| 5,863,794 A | 1/1999 | Strayer | 435/320.1 |
| 5,880,261 A | 3/1999 | Waeber et al. | 530/350 |
| 5,885,971 A | 3/1999 | German et al. | 514/44 |
| 5,952,221 A | 9/1999 | Kurtzman et al. | 435/320.1 |
| 5,997,859 A | 12/1999 | Barber et al. | |
| 6,066,624 A | 5/2000 | Woo et al. | |
| 6,217,860 B1 | 4/2001 | Woo et al. | |
| 6,241,982 B1 | 6/2001 | Barber et al. | |

FOREIGN PATENT DOCUMENTS

| | | | |
|---|---|---|---|
| WO | WO 95/05835 | 3/1995 | A61K/31/70 |

OTHER PUBLICATIONS

Ledley; Clinical Considerations in the Design of Protocols for Somatic Gene Therapy, 1991, Human Gene Therapy 2: 77–83.*

Eck et.al.; Gene–Based Therapy, 1990:77–100.*

Miller et.al.; Targeted vectors for gene therapy, 1995, FASEB J. 9: 190–199.*

Deonarain; Ligand–targeted receptor–mediated vectors for gene delivery, 1998, Ecp. Opin. Ther. Patents 8(1): 53–69.*

Verma et.al.; Gene therapy–promises, problems and prospects, 1997, Nature, vol. 389: 239–242.*

Crystal; Transfer of Genes to Humans: Early Lessons and Obstacles to Success, 1995, Science, vol. 270: 404–410.*

Romano et.al.; Gene Transfer Technology in Therapy: Current Applications and Future Goals, 1999, Stem Cells 17: 191–202.*

Welsh et.al.; Stimulation of pancreatic islet beta–cell replication by oncogenes, 1988, Proc. Natl. Acad.Sci., vol. 85: 116–120.*

Seljffers et.al.; Increase in PDX–1 Levels Suppressess Insulin Gene Expression in RIN 1046–38 Cells, 1999, Endocrinology, vol. 140: 3311–3317.*

Halloran et al., Gene therapy for pancreatic cancer—current and prospective strategies, 2000, *Surgical Oncology*, vol. 9, Elsevier, pp. 181–191.

Melloul et al., Regulation of insulin gene transcription, 2002, *Diabetologia*, Springer–Verlag, pp. 309–326.

Ray et al., Beta Cell–Specific Ablation of Target Gene Using Cre–loxP System in Transgenic Mice, 1999, *Journal of Surgical Research*, vol. 84, pp. 199–203.

Ray, et al., "Development of a Transgenic Mouse Model Using Rat Insulin Promoter to Drive the Expression of CRE Recombinase in a Tissue–Specific Manner," International Journal of Pancreatology, vol. 25, No. 3, Jun. 1999, pp. 157–163.

Crowe, et al., "Mutagenesis of the Rat Insulin II 5'–Flanking Region Defines Sequences Important for Expression in HIT Cells," Molecular and Cellular Biology, vol. 9, No. 4, Apr. 1989, pp. 1784–1789.

Tirone, et al., "β Cell Specific Cytotoxicity Using a Rat Insulin Promoter Thymidine Kinase Construct," *Association for Academic Surgery–Abstracts*, 33rd Annual Meeting, Philadelphia, PA, Nov. 18–20, 1999, pp. 287–288.

Tirone, et al., "Alterations in Insulin Secretion in the Somatostatin Subtype Receptor 5 Knockout Mouse Using the Isolated Perfused Mouse Pancreas Model," *Surgical Forum*, 86th Annual Clinical Congress 2000, vol. LI, Oct. 2000, pp. 44–46.

Tirone, et al., "PANC–1 Cells Can Be Targeted In Vitro with a Rat Insulin Promoter Thymidine Kinase Construct," *Society for Surgery of the Alimentary Tract*, 41st Annual Meeting at Digestive Disease Week, 2794, SSAT/Ross Residents' Conference, San Diego, CA, May 20, 2000 (2 pp).

Fagan, et al., "Insulin secretion is inhibited by subtype five somatostatin receptor in the mouse," Surgery, vol. 124, No. 2, 1998, pp. 254–259.

(List continued on next page.)

Primary Examiner—Deborah Crouch
Assistant Examiner—Thaian N. Ton
(74) Attorney, Agent, or Firm—Jenkens & Gilchrist

(57) ABSTRACT

This invention relates to a recombinant nucleic acid for an RIP-tk (rat insulin promoter-thymidine kinase) construct that selectively targets insulin secreting cells, such as β-cells, PDX-1 positive human pancreatic ductal carcinomas, and other cells containing certain transcription factors. The present invention is useful in the treatment of pancreatic cancers, such as β-cell insulinomas.

3 Claims, 9 Drawing Sheets

OTHER PUBLICATIONS

Ray, et al., "A Mouse Model for Beta Cell–Specific Ablation of Target Gene(s) Using the Cre–loxP System," Biochemical and Biophysical Research Communications, 1998, 253:65–69.

Kleinman, et al., "Differential Inhibition and Islet Amyloid Polypeptide Secretion by Intraislet Somatostatin in the Isolated Perfused Human Pancreas," Pancreas, vol. 19, No. 4, Nov. 1999, pp. 346–352.

Atiya, et al., "Intraislet Somatostatin Inhibits Insulin (Via a Subtype–2 Somatostatin Receptor) But Not Islet Amyloid Polypeptide Secretion in the Isolated Perfused Human Pancreas," Journal of Gastrointestinal Surgery, vol. 1, No. 3, 1997, pp. 251–256.

Moldovan, et al., "Cloning of the Mouse SSTR5 Gene," Journal of Surgical Research, 1998, 76:57–60.

Ren, et al., "Activation of Human Somatostatin Receptor Type 2 Causes Inhibition of Cell Growth in Transfected HEK293 but Not in Transfected CHO Cells," Journal of Surgical Research, 1997, 71:13–18.

Kleinman, et al., "Regulatory Role of Intraislet Somatostatin on Insulin Secretion in the Isolated Perfused Human Pancreas," Pancreas, vol. 9, No. 2, 1994, pp. 172–178.

Ahlgren, et al., "β–cell–specific inactivation of the mouse Ipf1/Pdx1 gene results in loss of the β–cell phenotype and maturity onset diabetes," Genes & Development, 1998, 12:1763–1768.

Al–Hendy, et al., "Applying the Herpes Simplex Virus Thymidine Kinase/Ganciclovir Approach to Ovarian Cancer: An Effective in vitro Drug–Sensitization System," Gynecologic and Obstetric Investigation, 1997, 43:268–275.

Bonnekoh, et al., "Inhibition of Melanoma Growth by Adenoviral Mediated HSV Thymidine Kinase Gene Transfer In Vivo," The Journal of Investigative Dermatology, 1995, 104:313–317.

Chen, et al., "Gene Therapy for brain tumors: Regression of experimental gliomas by adenovirus–mediated gene transfer in vivo," Proc. Natl. Acad. Sci. USA, 1994, 91:3054–3057.

Dimaio, et al., "Directed enzyme pro–drug gene therapy for pancreatic cancer in vivo," Surgery, vol. 116, No. 2, 1994, pp. 205–213.

Eastham, et al., "Prostate Cancer Gene Therapy: Herpes Simplex Virus Thymidine Kinase Gene Transduction Followed by Ganciclovir in Mouse and Human Prostate Cancer Models," Human Gene Therapy, 1996, 7:515–523.

Frazier, "Gene Expression in Pancreatic Adenocarcinoma," Annals New York Academy of Sciences, 1999, 880:1–4.

Hamaguchi, et al., "NIT–1, a Pancreatic β–Cell Line Established From a Transgenic NOD/Lt Mouse," Diabetes, 1991, 40:842–849.

Hardy, et al., "Construction of Adenovirus Vectors through Cre–Lox Recombination," Journal of Virology, vol. 71, No. 3, 1997, pp. 1842–1849.

Katabi, et al., "Hexokinase Type II: A Novel Tumor–Specific Promoter for Gene–Targeted Therapy Differentially Expressed and Regulated in Human Cancer Cells," Human Gene Therapy, 1999, 10:155–164.

Kaneko, et al., "Adenovirus–mediated Gene Therapy of Hepatocellular Carcinoma Using Cancer–specific Gene Expression," Cancer Research, 1995, 55:5283–5287.

Kijima, et al., "Application of the Cre Recombinase/loxP System Further Enhances Antitumor Effects in Cell Type–specific Gene Therapy against Carcinoembryonic Antigen–producing Cancer," Cancer Research, 1999, 59:4906–4911.

Kumar, et al., "Subtype–Selective Expression of the Five Somatostatin Receptors (hSSTR1–5) in Human Pancreatic Islet Cells: A Quantitative Double–Label Immunohistochemical Analysis," Diabetes 1999, 48:77–85.

Lieber, et al., "Establishment of a Continuous Tumor–Vell Line (PANC–1) from a Human Carcinoma of the Exocrine Pancreas," Int. J Cancer, 1975, 15:741–747.

Naya, et al., "Diabetes, defective pancreatic morphogenesis, and abnormal enteroendocrine differentiation in BETA2/NeuroD–deficient mice," Genes & Development, 1997, 11:2323–2334.

Osaki, et al., "Gene Therapy for Carcinoembryonic Antigen–producing Human Lung Cancer Cells by Cell Type–specific Expression of Herpes Simplex Virus Thymidine Kinase Gene," Cancer Research, 1994, 54:5258–5261.

Robertson, et al., "Use of tissue–specific promoter for targeted expression of the herpes simplex virus thymidine kinase gene in cervical carcinoma cells," Cancer Gene Therapy, vol. 5, No. 5, 1998, pp. 331–336.

Sander, et al., "The β cell transcription factors and development of the pancreas," J. Mol Med., 1997, 75(5):327–340 (14 pp).

Schwartz, et al., "An orthotopic in vivo model of human pancreatic cancer," Surgery vol. 126, No. 3, 1999, pp. 562–567.

Siders, et al., "Melanoma–specific cytotoxicity induced by a tyrosinase promoter–enhancer/herpes simplex virus thymidine kinase adenovirus," Cancer Gene Therapy vol. 5, No. 5, 1998, pp. 181–291.

Smyth–Templeton, et al., "Improved DNA: liposome complexes for increased systemic delivery and gene expression," Nature Biotechnology, 1997, 15:647–652.

St–Onge, et al., "Pancreas development and diabetes," Current Opinion in Genetics Development 1999, 9:295–300.

Strowski, et al., "Somatostatin Inhibits Insulin and Glucagon Secretion via Two Receptor Subtypes: An in Vitro Study of Pancreatic Islets from Somatostatin Receptor 2 Knockout Mice," Endocrinology, vol. 141, No. 1, 2000, pp. 111–117.

Tanaka, et al., "Adenovirus–Mediated Gene Therapy of Gastric Carcinoma Using Cancer–Specific Gene Expression in Vivo," Biochemical and Biophysical Research Communications, 1997, 231:775–779.

Tong, et al., "In Vivo Gene Therapy of Ovarian Cancer by Adenovirus–Mediated Thymidine Kinase Gene Transduction and Ganciclovir Administration," Gynecologic Oncology, 1996, 61:175–179.

Vandier, et al., "Selective Killing of Glioma Cell Lines Using an Astrocyte–specific Expression of the Herpes Simplex Virus–Thymidine Kinase Gene," Cancer Research, 1998, 58:4577–4580.

Tong, et al., "Adenovirus–Mediated Thymidine Kinase Gene Transduction in Human Epithelial Ovarian Cancer Cell Lines Followed by Exposure to Ganciclovir," Anticancer Research, 1996, 16:1611–1617.

* cited by examiner p<0.05 via student t-test, n=48 per construct

SEQUENCE LISTING

<160> NUMBER OF SEQ ID NOS: 15

<210> SEQ ID NO 1
<211> LENGTH: 502
<212> TYPE: DNA
<213> ORGANISM: Rattus rattus

<400> SEQUENCE: 1

```
aattctgctt tccttctacc tctgagggtg agctggggtc tcagctgagg tgaggacaca      60
gctatcagtg ggaactgtga acaacagtt caagggacaa agttactagg tcccccaaca     120
actgcagcct cctggggaat gatgtggaaa aatgctcagc caaggacaaa gaaggcctca    180
ccctctctga dacaatgtcc cctgctgtga actggttcat caggccaccc aggagcccct    240
cttaagactc taattaccct aaggctaagt agaggtgttg ttgtccaatg agcactttct    300
gcagacctag caccaggcaa gtgtttggaa actgcagctt cagcccctct ggccatctgc    360
tgatccaccc ttaatgggac aaacagcaaa gtccagggt caggggggg gtgctttgga     420 ctataaagct agtggggatt cagtaacccc cagccctaag tgaccagcta cagtcaggaa    480
accatcagca agcaggtatg ta                                              502
```

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence:Synthetic
<221> NAME/KEY: modified_base
<222> LOCATION: (3)..(4)
<223> OTHER INFORMATION: N = A, C, T, or G

<400> SEQUENCE: 2

```
canntg                                                                  6
```

<210> SEQ ID NO 3
<211> LENGTH: 4
<212> TYPE: DNA
<213> ORGANISM: Artificial Sequence
<220> FEATURE:
<223> OTHER INFORMATION: Description of Artificial Sequence:Synthetic

<400> SEQUENCE: 3

```
taat                                                                    4
```

<210> SEQ ID NO 4
<211> LENGTH: 6
<212> TYPE: DNA
<213> ORGANISM: Artificial Sequence
<220> FEATURE:
<223> OTHER INFORMATION: Description of Artificial Sequence:Synthetic

<400> SEQUENCE: 4

```
cttaat                                                                  6
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 5
tgaacagtga ggagcagtac                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 6
ttttccactt catgcgacgg                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 7
cgccgagttt gaaaaaaatt                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 8
tttttccgac ggaagacatt                                               20

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:Synthetic

<400> SEQUENCE: 9
ttggccatct gctgatccac ccttaatggg ac                                 32

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 10
gggaacgcca cacagtgcca                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 11 gtacccttc cgtcgacctg                                                20

<210> SEQ ID NO 12
<211> LENGTH: 6
<212> TYPE: DNA
<213> ORGANISM: Artificial Sequence

```
<220> FEATURE:
<223> OTHER INFORMATION: Description of Artificial Sequence:Synthetic

<400> SEQUENCE: 12 ctcccc                                                                    6

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence:Synthetic

<400> SEQUENCE: 13 atatac                                                                    6

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:Synthetic

<400> SEQUENCE: 14
gaaagctttc tgctttcctt ctacctc                                            27

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence:Synthetic

<400> SEQUENCE: 15
tctagagctt ggactttgct gtttgtcccg tatatggtgg atcagcag                     48
```

TREATMENT OF PANCREATIC ADENOCARCINOMA BY CYTOTOXIC GENE THERAPY

CROSS REFERENCE TO RELATED APPLICATIONS

This application claims the benefit of U.S. Provisional Patent Application No. 60/161,109, filed Oct. 22, 1999, and entitled "Promoter Driven Tissue Specific Cytotoxic Agents" and U.S. Provisional Patent Application No. 60/224,382, filed Aug. 9, 2000, and entitled "Promoter Driven Tissue Specific Cytotoxic Agents and Methods of Use."

BACKGROUND

1. Field of the Invention

This invention relates to selective targeting of cells with cytotoxic genes using fingerprinting promoter driven specific cytotoxic genetic constructs and transcription factors, and to methods for using these constructs and transcription factors to treat diseases of the pancreas, and, in particular, to an RIP-tk (rat insulin promoter-thymidine kinase) construct that selectively targets insulin secreting cells, such as beta (β) cells, and certain human pancreatic ductal carcinoma cells, to cause cell death.

2. Description of the Background

β-cell adenomas (insulinomas) are the most common of the islet cell tumors. Ninety percent of β-cell tumors are benign, however morbidity associated with their removal is significant. Malignant insulinomas have a 63% five-year recurrence rate with an average survival less than four years (Proye, C, 68 *Aust. N.Z.J. Surg.* 90–100 (1998)). Furthermore, there is no effective medical treatment for the devastating symptoms associated with hyperinsulinemia as a result of either insulinoma or nesidioblastosis (idiopathic hyperinsulinemia). Pancreatic ductal adenocarcinoma (PDA) likewise remains a devastating disease with a less than three percent five year survival rate.

Over 28,000 patients will be diagnosed with pancreatic cancer this year of which over 27,000 will die of their disease within five years (Yeo Cj, et al., Neoplasms of the Pancreas Exocrine Tumors in *Sabiston Textbook of Surgery* 1171–1175 (Sabiston D C, et al. eds., 1997)). The majority of pancreatic tumors arise from ductular cells, resembling cells found in the early embryonic pancreas. Currently, only surgery offers any chance for a cure and the majority of the time the cancer has spread before it is detected.

Cancer specific promoters are being identified and are being used in an effort to modify the expression of thymidine kinase in tumor cells (Tanaka T, et al., 231 *Biochemical and Biophysical Research Communications* 775–779 (1997); DiMaio J, et al., 116[2] *Surgery* 205–213 (1994); Osaki T, et al., 54 Cancer Research 5258–5261 (1994); Kaneko S, et al., 55 Cancer Research 5283–5287 (1995); Robertson M, et al., 5[5] *Cancer Gene Ther.* 331–336 (1998); Siders W, et al., 5[5] *Cancer Gene Ther.* 181–291 (1998); Vandier D, et al., 58 *Cancer Research* 4577–4590 (1998)). However, these therapies have limitations due to either the weakness of the promoter or the tissue specificity of its activation. The herpes simplex thymidine kinase (HSVtk) gene, under the transcriptional control of a ubiquitous promoter, has been introduced into a host and caused significant cell death in the presence of ganciclovir (Bonnekoh B, et al., 104 *The Journal of Investigative Dermatology* 313–317, (1995); Al-Hendy A, et al., 43 *Gynecologic and Obstetric Investigation* 268–275 (1997); Eastham J, et al., 7 Human Gene Therapy 515–523 (1996); Chen S-H, et al., 91 *Proc. Natl. Acad. Sci. USA* 3054–3057 (1994); Tong X, et al., 61 *Gynecologic Oncology* 175–179 (1996). Ganciclovir (GCV), an analogue of guanosine, requires both mammalian and viral tk to become active. In viral thymidine kinase containing cells, GCV is phosphorylated into an intermediate that kills dividing cells by inhibiting DNA synthesis and acting as a chain terminator (Mathews T, et al., 10 *Rev Infect Dis*. 180–192 (1992); Moolten F L, 50 *Cancer Res.* 7820–7825 (1986)). However, thymidine kinase with a ubiquitous promoter is not cell specific, limiting its use as a cytotoxic agent.

With the identification of tissue specific promoters, one can target therapies and selectively turn on genes in specific cell types, important goals in gene therapy. Cell specific strategies depend on a cell specific promoter that can activate the suicide gene only in the targeted tumor. To accomplish this, activation of the promoter-suicide construct should require the presence of transcription factors in the targeted tumor that will activate the promoter. In addition, an effective gene delivery system is needed. However, prior to the present invention, a method to express selected genes solely in β cells and other cells of pancreatic origin had not been developed. Such a method would provide a useful tool for development of treatment for insulinoma, nesidioblastosis and other pancreatic cancers.

Currently, there is no effective treatment for pancreatic β-cell tumors or pancreatic ductal adenocarcinomas. Consequently, there is a need for an effective and selective treatment for these diseases, as well as other diseases due to abnormal pancreatic cells.

SUMMARY OF THE INVENTION

The present invention overcomes the problems and disadvantages associated with current strategies and designs and provides a novel recombinant nucleic acid comprising an RIP-tk construct useful for the selective targeting and ablation of cells, such as cells comprising one or more specific transcription factors. The invention is particularly useful for the treatment of pancreatic cancer and other diseases of or affecting the pancreas.

Accordingly, one embodiment of the invention is directed to a method for selectively expressing a target gene in a pancreatic cell comprising delivering to the cell an effective amount of an agent containing a recombinant nucleic acid sequence, the sequence comprising an insulin promoter, such as a rat insulin promoter, operatively linked to the target gene. The cell may naturally contain or be cotransfected with one or more insulin promoter transcription factors selected from the group consisting of BETA2, GATA4, E47 and PDX-1.

Another embodiment of the invention is directed to a method for selectively ablating pancreatic cells in an individual comprising administering to the individual an effective amount of an agent comprising a recombinant nucleic acid sequence. The recombinant nucleic acid sequence preferably comprises a cytotoxic gene operatively linked to an insulin promoter, such as the rat insulin promoter. The pancreatic cells preferably express one or more transcription factors selected from the group consisting of BETA2, GATA4, E47 and PDX-1. Preferably, the cytotoxic gene is a nucleic acid encoding viral thymidine kinase (tk), and the method further comprises the step of administering ganciclovir, acyclovir, FIAU or 6-methoxypurine arabinoside to the individual in an amount effective to ablate the cells.

Another embodiment is directed to a method for selectively ablating a target in an individual comprising transfecting the individual with an agent comprising a recombinant nucleic acid sequence comprising a thymidine kinase gene operatively linked to an insulin promoter, such as a rat insulin promoter, and administering to the individual an effective amount of ganciclovir, acyclovir, FIAU or 6-methoxypurine arabinoside in an amount sufficient to cause ablation of the target. Preferably, the target comprises cells that naturally express or are cotransfected with one or more rat insulin promoter transcription factors selected from the group consisting of BETA2, GATA4, E47 and PDX-1.

Another embodiment is directed to a method for the production of a protein in a cell comprising delivering a nucleic acid molecule to the cell, wherein the nucleic acid molecule comprises an insulin promoter operatively linked to a structural nucleic acid sequence encoding the protein, and the cell comprises the PDX-1 transcription factor after delivery of the nucleic acid molecule.

Another embodiment of the invention is directed to a method for ablating cells in an individual comprising delivering an agent to the individual, wherein the agent comprises a nucleic acid molecule, and the nucleic acid molecule comprises an insulin promoter operatively linked to a structural nucleic acid sequence encoding a cytotoxic protein.

Another embodiment of the invention is directed to a method for treating a metabolic disease, such as hypoglycemia or hyperinsulinemia, in an individual comprising administering to the individual an effective amount of an agent comprising a recombinant nucleic acid sequence comprising a cytotoxic gene operatively linked to an insulin promoter. Preferably, the cytotoxic gene encodes thymidine kinase and the method further comprises the step of administering to the individual an agent, such as ganciclovir.

Another embodiment of the invention is directed to a method of treating a metabolic disease in an individual comprising delivering an agent to the individual, wherein the agent comprises a nucleic acid molecule, and the nucleic acid molecule comprises an insulin promoter operatively linked to a structural nucleic acid sequence encoding a cytotoxic protein.

Another embodiment is directed to a composition for selectively causing regression or ablation of a pancreatic cell comprising a recombinant nucleic acid sequence which comprises a thymidine kinase gene operatively linked to an insulin promoter, such as the rat insulin promoter.

Another embodiment of the invention is directed to an isolated nucleic acid molecule comprising an insulin promoter operatively linked to a structural nucleic acid sequence encoding a cytotoxic protein.

Another embodiment of the invention is directed to a kit comprising an isolated nucleic acid molecule, wherein the isolated nucleic acid molecule comprises an insulin promoter operatively linked to a structural nucleic acid sequence encoding a cytotoxic protein. Preferably, the nucleic acid molecule is contained in a first container, and the kit further comprises one or more agents selected from the group consisting of ganciclovir, acyclovir, FIAU, and 6-methoxypurine arabinoside contained in the same or a second container.

Another embodiment of the invention is directed to a method for increasing the secretion of insulin in an individual comprising reducing the concentration of the somatostatin receptor.

Other embodiments and advantages of the invention are set forth in part in the description which follows, and in part, will be obvious from this description, or may be learned from the practice of the invention.

DESCRIPTION OF THE SEQUENCE LISTINGS

Figure 1A:
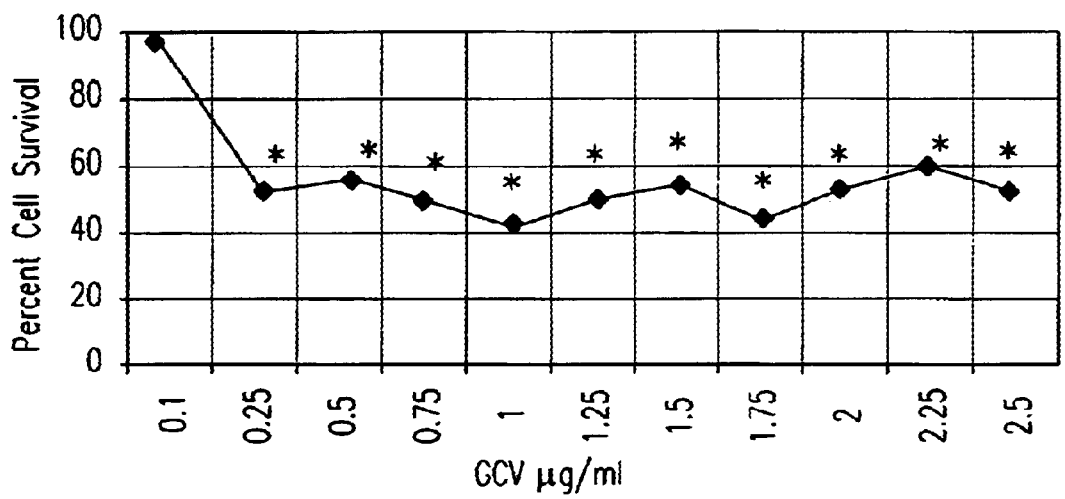
FIG. 1A is a dose response curve for NIT-1 cells given GCV.

The following sequence listings form part of the present specification and are included to further demonstrate certain aspects of the present invention. The invention may be better understood by reference to one or more of these sequences in combination with the description of the invention presented herein.

SEQ ID NO:1 is a fragment of the rat insulin promoter.
SEQ ID NO:2 is the BETA-2 site CANNTG.
SEQ ID NO:3 is the PDX-1 site TAAT.
SEQ ID NO:4 is the PDX-1 binding site CTTAAT.
SEQ ID NO:5 is the mouse PDX-1 primer forward bps 281–300.
SEQ ID NO:6 is the mouse PDX-1 primer reverse bps 1227–1201.
SEQ ID NO:7 is primer forward bps 944–964 specific for both human and mouse BETA2 RNA.
SEQ ID NO:8 is primer reverse bps 1227–1207 specific for both human and mouse BETA2 RNA.
SEQ ID NO:9 is a probe containing a BETA-2 site and a PDX-1 site.
SEQ ID NO:10 is primer forward bps 192–210 for human PDX-1 RNA.
SEQ ID NO:11 is primer reverse bps 644–624 for human PDX-1 RNA.
SEQ ID NO:12 is PDX-1 binding site CTCCCC.
SEQ ID NO:13 is PDX-1 binding site ATATAC.

SEQ ID NO:14 is a primer adding a HindIII restriction site.
SEQ ID NO:15 is a primer adding a BglII restriction site.

DESCRIPTION OF THE INVENTION

As embodied and broadly described herein, the present invention is directed to selective targeting of pancreatic cells with cytotoxic genes using promoter driven specific cytotoxic genetic constructs and transcription factors, and to methods for using these constructs and transcription factors to treat cancer and other diseases.

Specifically, the present invention is directed to an RIP-tk (rat insulin promoter-thymidine kinase) construct that selectively targets insulin secreting cells, such as beta (β) cells and certain human pancreatic ductal carcinoma cells (PDX-1 positive), to cause cell death.

Currently, there is no effective medical treatment for pancreatic β-tumors or insulinomas. Existing therapies which employ promoter-thymidine kinase constructs are not tumor-specific, which limits their efficacy. It has been discovered that by using an insulin promoter coupled to a suicide gene, the efficacy of pancreatic β-cell tumor gene therapy may be greatly increased. The present invention is useful for treatment of insulin secreting tumors as well as in the development of new adjuvant gene therapies for patients with pancreatic β-cell tumors or insulinomas. The invention may also be used to treat PDX-1 positive pancreatic ductal cancers and hypoglycemia.

The present invention demonstrates that pancreatic tumor specific cytotoxicity can be achieved through the use of promoter specific gene therapy. For example, it has been discovered that the rat insulin promoter coupled to the thymidine kinase gene can be used with GCV to specifically cause cell cytotoxicity in a mouse insulinoma (NIT-1) cell line and in PDX-1 positive human pancreatic ductal cancer cells. By coupling rat insulin promoter to a suicide gene, mouse insulinoma cell line (NIT-1 cells) were ablated both in vitro and in vivo with GCV. Similar results were achieved with PDX-1 positive human pancreatic ductal cancer cells. As such, it has been discovered that by operatively linking a suicide gene, such as thymidine kinase, to an insulin promoter, the thymidine kinase gene will be selectively activated in β-cell tumors and certain pancreatic ductal cancers, thereby causing tumor cell death.

Furthermore, the cytotoxic effect of RIP-tk may be enhanced in the presence of RIP transcription factors such as, for example, PDX-1, BETA2, GATA4, and E47. These transcription factors increase the efficiency of RIP, and are useful in studies of how the promoter works.

As indicated in greater detail in the examples below, it has been or will be shown that: a) rat insulin promoter (RIP) will drive the expression of the reporter gene β-galactosidase (lacZ), in vitro, in a mouse insulinoma cell line (NIT-1) and in human pancreatic ductal adenocarcinoma cell lines (PANC-1, CAPAN-1); b) NIT-1, PANC-1 and CAPAN-1 specific ablation can be achieved in vitro using thymidine kinase coupled to RIP (RIP-tk) followed by ganciclovir (GCV) treatment; c) RIP transcription factor BETA2 regulates the expression of RIP-tk in NIT-1 cells while PDX-1 regulates expression in human pancreatic ductal carcinoma (CAPAN-1 and PANC-1) cell lines; d) the cytotoxic effect of RIP-tk in vitro can be enhanced by cotransfection of RIP transcription factors, BETA2, GATA4, PDX-1 and E47; e) RIP will drive the expression of lacZ in a mouse insulinoma model and in a PDX-1 positive human pancreatic ductal carcinoma mouse model in vivo; f) insulinoma-specific ablation can be achieved in vivo using the RIP-tk gene followed by GCV treatment; and g) RIP-tk followed by GCV treatment can be used to ablate PDX-1 positive human pancreatic ductal carcinoma in vivo.

β-Cell Specific Cytotoxicity Using a Rat Insulin Promoter—Thymidine Kinase Construct It has been discovered that a RIP-tk construct may be used to selectively target β-cells. The rat insulin promoter (RIP) is a strong cell specific promoter that is activated in cells that produce insulin. It has been discovered that by incorporating RIP into a construct with the suicide gene, thymidine kinase gene (tk), both in vitro and in vivo β-cell specific cytotoxicity may be achieved, and that such constructs may be used to selectively kill proliferating β-cells, preventing hypoglycemia and animal death.

The rat insulin promoter (RIP; see Crowe D et al., 9 *Molec Cell Biol* 1784–1789 (1989); Ray M, et al., 25 *Int J Pancreatology* 157–163 (1999)) was studied to determine its usefulness to selectively target NIT-1 cells (mouse beta (β) cell tumor line derived from the non-obese diabetic mouse (Hamaguchi D, et al., 40 *Diabetes* 842–844 (1991)) and to determine the transcription factors responsible for NIT-1 cell specific activation of RIP. In addition, the effect of the RIP-tk construct on both blood glucose levels and life expediency in mice inoculated with NIT-1 cells was evaluated.

As shown in Examples 1, 5 and 6, below, the data confirm that the RIP is a β-cell specific promoter. It has been discovered that β-cell specific cytotoxicity can be accomplished and β cells can be selectively targeted for destruction using RIP coupled to the suicide gene, thymidine kinase. Further, animals can be rescued from the devastating effects of hypoglycemia induced by β cell adenomas (NIT-1 cells) using such constructs.

It has been determined that 0.502 kb of RIP (SEQ ID NO:1) contains elements to maximally drive the expression of a gene. These elements include six BETA-2 sites (CANNTG; SEQ ID NO:2) and three PDX-1 sites (TAAT; SEQ ID NO:3), one of which contains the sequence CTTAAT (SEQ ID NO:4), which is the most favorable PDX-1 binding sequence. This smaller fragment allows for the development of smaller constructs. Such fragments make the creation of the constructs technically easier, increase the transfection efficiency in vitro, and aid in the development of in vivo gene delivery systems.

In an initial study, RIP was used to drive expression of the lacZ gene in a variety of cell lines, including NIT-1, F9, 3T3, H411 and CV1 cells. NIT-1 cells form β-cell tumors when injected into the peritoneum of mice with the mice dying of hypoglycemia within one hundred days. Mouse embryonic carcinoma cell line F9, mouse fibroblast cell line 3T3 and mouse lung cell line H411 were chosen as control cells because they represent a variety of rodent cell types. Monkey renal CV-1 cells were also included as a control to represent a higher mammalian species.

Despite the variety of cell types, as shown in Examples 1 and 5, the RIPlacZ gene failed to display any lacZ gene expression in any of the control cells, despite staining using the RSVlacZ gene in the same cells. However, in NIT-1 cells, the RIPlacZ gene consistently expressed beta-galactosidase protein, confirming that RIP is a β-cell specific promoter. In addition, significant decrease in cell survival was observed in NIT-1 cells transfected with RIP-tk, in vitro ($p<0.05$, $n=48$).

RT/PCR was performed looking for the transcription factors BETA-2 and PDX-1 because they have been shown to be responsible for activation of the rat insulin promoter in the islets of a rat (Sander M, et al., 75 *Mol Med.* 327–340 (1997)). Messenger RNA for both BETA2 and PDX-1 was found in NIT-1 cells.

Because the mere presence of mRNA for either BETA-2 or PDX-1 in the cells under study does not prove that they are responsible for RIP activation, EMSA were performed with an oligonucleotide that contained both a BETA-2 site and a PDX-1 site. A supershift was observed for both BETA2 and PDX-1. Specifically, supershift analysis with both BETA-2 and PDX-1 antibodies substantiated that these two transcription factors are in part responsible for RIP activation in NIT-1 cells.

In vivo studies were also performed. In one study, NIT-1 cell tumors were successfully targeted with the RIPlacZ gene. In addition, mice innoculated with NIT-1 cells developed clinically relevant tumors with hypoglycemia and death at sixty days post innoculation. However, the in vivo delivery of the RIP-tk gene in combination with GCV inhibited hypoglycemia and animal death (n=30, p<0.05).

In sum, the data demonstrate that a β-cell tumor line can be targeted, in vitro and in vivo, for genetic manipulation using the rat insulin promoter. As shown in the examples, only the beta (NIT-1) cells stained blue after X-gal staining (p<0.05, n=16) or had detectable levels of beta-galactosidase protein (p<0.05, n=6) in vitro. The RIP-tk genetic construct resulted in NIT-1 specific cytoxicity. F9 cells demonstrated no decrease in cell survival with the RIP-tk gene suggesting that there was no transcription of the thymidine kinase gene with the rat insulin promoter in F9 cells. RIP-tk in combination with GCV inhibited hypoglycemia and death in mice with NIT-1 tumors. Thus, the rat insulin promoter may be used to achieve β-cell specific cytoxicity with the tissue specific activation of thymidine kinase.

PDX-1 Positive Human Pancreatic Ductal Carcinoma Cells can be Targeted Using a RIP-tk Construct It has also been discovered that a RIP-tk construct may be used to target PDX-1 positive human pancreatic ductal carcinoma cells. As used herein, "PDX-1 positive" means cells that naturally contain or comprise, or are modified to contain or comprise, a PDX-1 transcription factor.

The adult mammalian pancreas is composed of two distinct glands with different functions: the islets and the exocrine glands. However, there exists increasing evidence that these cell types originate from a single cell early in embryonic development (St-Onge L, et al., 9(3) *Curr Opin Genet Dev.* 295–300, (1999)). PDX-1 both plays an important role in early pancreatic development and in β-cell specific activation of the insulin promoter in mature islets. (Ahlgren U, et al., 12(12) *Genes Dev.* 1763–1768 (1998)).

Pancreatic ductal carcinoma resembles cells found early throughout the embryologic pancreas. Human ductal pancreatic adenomcarcinoma (PDA) cells are hypothesized to arise from a pluri-potential stem cell. It has been determined that these cells contain the transcription factor PDX-1. Although PDX-1 plays an important role in embryonic pancreatic development, it is normally found only in the mature islets and activates the insulin promoter. Following investigation, it was discovered that human pancreatic ductal carcinoma cell lines could also be targeted both in vivo and in vitro using the rat insulin promoter (RIP) to drive the suicide gene thymidine kinase (tk). In addition, the transcription factor (PDX-1) responsible for insulin promoter activation in these cells was identified.

Specifically, it was hypothesized that human pancreatic ductal carcinoma cell lines retain their ability to produce the transcriptional machinery needed to activate the insulin promoter. To confirm this, the rat insulin promoter (RIP) was studied to determine if it could selectively target human pancreatic ductal carcinoma cells for genetic manipulation in culture using the suicide gene thymidine kinase (tk) followed by ganciclovir (GCV). Experiments were also undertaken to identify the transcription factor(s) responsible for insulin promoter activation in these cancer cells. The insulin promoter's activation is normally limited to β-cells and a genetic construct containing the suicide gene thymidine kinase driven by RIP should only effect dividing cells with the transcriptional machinery available to activate the insulin promoter.

The resulting data as shown in Examples 2–4, indicate that the RIP-tk gene is able to target PDX-1 positive human pancreatic ductal carcinoma cells (both PANC-1 and CAPAN-1 cells), in vitro and in vivo, and further, that cell-specific cytotoxicity of human pancreatic ductal carcinoma cells can be achieved using a RIP thymidine kinase construct and GVC in vitro and in vivo. The data also indicate that the transcription factor PDX-1, important in early embryonic pancreatic development, is responsible for both the activation and the targeting of the rat insulin promoter in PDA cells. In addition, a liposomal gene delivery system was shown to be effective in vivo in scid mice.

In the development of the RIP-tk and RIPlacZ genetic constructs, the 0.502 kb that is useful for maximal transcription of a gene was used (Frazier M L, 880 *Annals New York Academy of Sciences* 1–4 (1999)). As noted, these 502 base pairs contain six E box binding sites for the transcription factor BETA2 and three PDX-1 binding sites, of which only one contains the most favorable PDX-1 binding sequence (CTTAAT). Both BETA2 and PDX-1 are found and are responsible for insulin promoter activation in rodents and humans, however BETA2 appears to play a dominant role in rodents while PDX-1 is dominant in humans (Frazier M L, 880 *Annals New York Academy of Sciences* 1–4 (1999)).

A number of cell types were used in the study. PANC-1, CAPAN-1, and MIA-1 cells are all human pancreatic ductal carcinoma cell lines derived from three different humans (Lieber M, et al., 15(5) *Int. J Cancer* 741–7 (1975)). These cells form clinically relevant pancreatic ductal cell tumors when injected into the peritoneum of mice (Schwartz R E, et al., 126(3) *Surgery* 562–567 (1999)). Human small cell lung carcinoma cell line A549, and human breast carcinoma cell line (T47D) were also chosen as control cancer cell lines because they represent a variety of undifferentiated human tissues.

To determine whether these cell lines contained RIP activating promoters, RT/PCR was performed on whole RNA isolated from PANC-1, CAPAN-1, and MIA-1 cells looking for the presence of known RIP transcription factors BETA-2 and PDX-1. BETA-2 was chosen because it appears to be the dominant transcription factor in rodents and therefore responsible for the majority of the activation of RIP in these animals (Naya F J, et al., 11 *Genes and Development* 2323–2334 (1997)). The 502 base pair RIP used in the experiment contain six E box binding sites for BETA2 and three PDX-1 sites. Message for PDX-1 was found in PANC-1 and CAPAN-1 cell lines but not in MIA-1. No message for BETA2 was found in any of the cell types.

As noted, PDX-1 is responsible both for early embryonic pancreatic development and for insulin promoter activation in the mature islet. Normally, it is not found outside the β-cell once the pancreas matures (St-Onge L, et al., 9(3) *Curr Opin Genet Dev.* 295–300 (1999); Ahlgren U, et al., 12(12) *Genes Dev.* 1763–1768 (1998); Frazier M L, 880 *Annals New York Academy of Sciences* 1–4 (1999)). Interestingly, a message for PDX-1 was discovered in the human pancreatic ductal carcinoma cell lines PANC-1 and CAPAN-1, but not in MIA-1.

To further demonstrate that PDX-1 is responsible for RIP activation in PANC-1 and CAPAN-1 cells, nuclear extract was obtained and assayed to see if any nuclear proteins bound to the PDX-1 binding site were found on RIP. Once binding was established, an antibody specific for PDX-1 was added to identify if the PDX-1 protein is the nuclear protein bound to RIP. The resulting data confirmed that the transcription factor PDX-1 is present in PANC-1 and CAPAN-1 cells and binds to RIP.

It was then hypothesized that RIP-driven cytotoxic constructs would work in PDX-1 postive cancer cell lines. This was confirmed as follows.

Utilizing a RIP-driven marker gene, RIPlacZ, only PANC-1 and CAPAN-1 demonstrated lacZ gene expression in vitro, whereas the other cell lines did not. All cell lines displayed lacZ gene expression using the ubiquitous promoter lacZ construct (RSVlacZ) (Table 1). These results supported the use of RIP as cell specific promoter to drive the expression of genes in PDX-1 positive human pancreatic ductal carcinoma cell lines.

The effectiveness of the cytotoxic gene contruct, RIP-tk, was studied in vitro and found to selectively kill PANC-1 and CAPAN-1 cells, but not the other cell lines. No killing of PANC-1 and CAPAN-1 was seen with in untransfected cells given GCV alone or with the use of a hollow vector. All cell lines demonstrated an increase in cell death with the RIP-tk gene governed by a ubiquitous promoter. These data demonstrate RIP-tk cell-specific cytotoxicity of PDX-1-positive, pancreatic cancer cell lines in vitro.

To confirm that PDX-1 was responsible for the in vitro effects, the PDX-1 binding site on the RIP was mutated. There are three PDX-1 binding sites, however the PDX-1 site (CTTAAT) was chosen because it is the dominant binding site and is close to the 3' end of the promoter, making it easier to mutate using PCR technology. LacZ gene expression in PANC-1 and CAPAN-1 cell lines transfected with the mutated RIPlacZ construct was negligible compared to that seen with the unmutated RIPlacZ construct. These data indicate that PDX-1 is useful for RIP activation of gene expression in these cell lines.

More specifically, as shown in Example 2, only the pancreatic ductal carcinoma cells PANC-1 turned blue after X-gal staining (p<0.05, n=32 per cell type) and only PANC-1 and CAPAN-1 cells had detectable levels of beta-galactosidase protein (p<0.05, n=16). A significant increase in cell death was observed in PANC-1 and CAPAN-1 cells transfected with RIP-tk, while no significant increase in cell death was observed in A549 or MIA-1 cells transfected with RIP-tk (p<0.05, n=32). PANC-1 and CAPAN-1 cells contained RNA for PDX-1, but not for BETA2. MIA-1 cells did not contain RNA for either PDX-1 or BETA2. A super shift was observed with the PDX-1 antibody and nuclear extract from both PANC-1 and CAPAN-1. Decreased levels of beta-galactosidase protein was found in PANC-1 and CAPAN-1 cells transfected with the mutated RiplacZ gene when compared to the wild type RIPlacZ gene (p<0.05, n=8).

The effectiveness of RIPlacZ and RIP-tk gene constructs against PANC-1 was then studied in vivo using a SCID mouse model. SCID mice are immunodeficient and will not reject a human pancreatic cancer cell line. PANC-1 cells were injected intraperitoneally and tumors were visible by day 24. Once the model was established in the laboratory, the mice were treated with the gene therapy beginning at day 24 post-tumor-injection. A liposomal gene-delivery system was chosen for simplicity and effectiveness (Schwarz R E, et al., 126(3) *Surgery* 562–567 (1999); Smyth-Templeton N, et al., 15 *Nature Biotechnology* 647–652 (1997)). The liposomal gene contruct was delivered intraperitioneally and mice were given GCV intraperitoneally twice per day for 14 days. Following treatment, mice were observed for 60 days and sacrificed.

At necropsy, all nine mice treated with the gene therapy/GCV had no visible pancreatic tumors and one of nine had microscopic tumors on the liver. All control groups had large tumors. These data confirm that human PANC-1 cells can be selectively killed using systemic delivery of RIP-tk/GCV gene therapy.

The resulting data supports the hypothesis that pancreatic ductal carcinoma represents a de-differentiated cell found early in embryological development containing properties found both in the exocrine pancreas and in the mature islet and therefore able to activate the insulin promoter. The data also demonstrates that RIP can be used to target certain human pancreatic ductal carcinoma cell lines in vivo and in vitro. The data demonstrates that the RIP-tk gene may be used with GCV to target and kill these cells. The data also indicates that the transcription factor PDX-1, important in early embryonic pancreatic development, is responsible for the activation of the rat insulin promoter in these cells.

Example 3, further corroborates that human ductal pancreatic adenocarcinoma (PDA) cells that contain the transcriptional machinery to activate RIP (e.g., PDX-1 positive) can be targeted with a RIP-tk gene. PDA cell lines CAPAN-1 (C-1) and MIA-1 (M-1) were evaluated to determine if they could be targeted using the rat insulin promoter (RIP) driving the thymidine kinase gene (tk). In addition, the transcription factors known to activate RIP in rodents (PDX-1 or BETA 2) were evaluated to determine which were responsible for RIP activation in human PDA cells.

As shown in Example 3, the resulting data provide further confirmation that RIP can drive the expression of a gene in human PDA cells (CAPAN-1), and that the transcription factor PDX-1 is useful for promoter activation in human PDA cells.

In sum, PDX-1 positive human pancreatic cancer-specific cytotoxicity was achieved both in vivo and in vitro using RIP to drive the suicide gene, thymidine kinase. RIP activation of these cell lines was shown to be regulated by the transcription factor, PDX-1.

Alterations in Insulin Secretion in the SSTR-5 Knock Out Mouse Using the Isolated Perfused Mouse Pancreas Model In addition, alterations in insulin secretion in the somatostatin subtype receptor 5 knock out mouse using the isolated perfused mouse pancreas model were studied. The inhibitory biological activities of somatostatin are mediated by five high affinity receptors that all have been identified in the islets of Langerhan. (Kumar U, et al., 48(1) *Diabetes* 77–85 (1999)). In mouse isolated islets, a SSTR-5 specific agonist inhibited insulin secretion, implicating SSTR-5's role in insulin homeostasis. (Fagen S P, et al., 124(2) *Surgery* 254–258(1998)). Recently, SSTR-2 has been shown to be involved in glucagon inhibition. (Strowski M Z, et al., 141(1) *Endocrinology* 111–7 (2000)).

The mouse SSTR-5 gene was cloned and ablated by homologous recombination to further elucidate its role in insulin homeostasis. Whole pancreata of young (three-month-old) and old (twelve-month-old) mice were isolated and perfused to determine the effect glucose stimulation has on insulin secretion in mice lacking the SSTR-5 gene over time.

As shown in Example 8, histological sections of islets suggest there is no difference in islet cell morphology between 3-month-old KO and 3-month-old wt mice or 12-month-old KO and 12-month-old wt mice. There were no differences in weight between KO and aged match controls. There were no differences in basal insulin secretion between any of the mice. Additionally, glucose stimulation caused in a significant increase in insulin secretion compared to basal in all mice. Three-month-old KO mice demonstrated a blunted first phase that was significant compared to all other mice (Table 8 and FIG. 7 ). Twelve-month-old KO mice demonstrated a significant augmentation of both first phase and second phase compared to all other groups (Table 8 and FIG. 7).

As such, the phenotype of the SSTR-5 KO mouse appears to be a blunted first phase in 3-month-old mice and an augmentation of glucose stimulated insulin secretion in 12-month-old mice. The data suggest that the SSTR-5 gene is involved in the regulation of glucose stimulated insulin secretion and has a limited role in basal insulin secretion. The data suggests that the genotypic loss of the SSTR-5 gene is partially compensated for in mice at three months of age. However, as the mice age to 12 months these compensatory mechanisms are no longer functional and an augmentation of glucose stimulated insulin secretion is seen. It may be concluded that SSTR-5 gene regulates glucose stimulated insulin secretion and alterations of insulin release occur in the perfused pancreata of both 3-month-old and 12-month-old SSTR-5 genetically ablated mice.

Accordingly, one embodiment of the invention is directed to a method for selectively expressing a target gene in a pancreatic cell. This method comprises the step of delivering to the cell an effective amount of an agent containing a recombinant nucleic acid sequence, the sequence comprising an insulin promoter operatively linked to the target gene. Although insulin promoters from various species of animals, including man, may be used in the practice of the invention, in a preferred embodiment, the insulin promoter is a rat insulin promoter.

The agent may be delivered to the cell using any suitable means, such as by cotransfection. In one embodiment, the agent is delivered by infecting with a recombinant viral vector, such as a recombinant adenovirus. For example, a gutless adenovirus may be prepared per the protocol of Hardy et al. (Smyth-Templeton N, et al., 15 *Nature Biotechnology* 647–652 (1997); Hardy S, et al., 71(3) *Journal of Virology*" 1842–1849 (1997)), or by using the gutless adenovirus available from the Shell Center for Gene Therapy, Baylor College of Medicine (Houston, Tex.).

Alternately, a liposomal gene delivery system may be used. For example, liposomal complexes, such as those available from the Shell Center for Gene Therapy, Baylor College of Medicine, may be used. Alternately, liposomal complexes may be prepared per the protocols of Schwarz R E, et al., 126(3) *Surgery* 562–567 (1999), and Smyth-Templeton N, et al., 15 *Nature Biotechnology* 647–652 (1997). Liposome gene constructs may be delivered using any suitable route of delivery, but in a preferred embodiment are delivered intraperitoneally.

The pancreatic cell is preferably one that expresses one or more transcription factors selected from the group consisting of BETA2, GATA4, E47 and PDX-1. If desired, the method may further comprise cotransfecting the cell with one or more insulin promoter transcription factors selected from the group consisting of BETA2, GATA4, E47 and PDX-1.

Pancreatic cells that may be targeted include PDX-1 positive pancreatic ductal carcinoma cells, β-cell tumor cells, insulinoma cells, and β-cells. Certain cell lines useful for research purposes may also be effectively targeted, including PANC-1 cells, CAPAN-1 cells, and NIT-1 cells.

The insulin promoter may be used to drive expression of any desired gene. However, in a preferred embodiment, the promoter is functionally linked to and drives expression of a gene encoding thymidine kinase. In this embodiment, the method further comprises the step of delivering to the cell GCV, acyclovir, FIAU or 6-methoxypurine arabinoside in an amount effective to ablate the cell.

Another embodiment of the invention is directed to a method for selectively ablating pancreatic cells in a patient comprising administering to the patient an effective amount of an agent comprising a recombinant nucleic acid sequence comprising a cytotoxic gene operatively linked to an insulin promoter.

In a preferred method, the cytotoxic gene is the nucleic acid encoding thymidine kinase, and the method further comprises the step of administering GCV, acyclovir, FIAU or 6-methoxypurine arabinoside to the patient in an amount effective to ablate the cells.

The present invention is not limited to thymidine kinase as the cytotoxic gene. As will be clear to those of skill in the art, various cytotoxic genes may be used. For example, the cytotoxic gene may be a directly cytotoxic gene, such as the gene encoding diphtheria toxin, the gene encoding ricin or the gene encoding caspase. Caspase is a gene product that promotes cell death by apoptosis. Alternately, the cytotoxic gene may be a suicide gene, such as the aforementioned gene encoding thymidine kinase. Suicide genes can make targeted cells susceptible to specific drugs. Administering the drug to cells carrying such suicide genes results in cell death. For example, cells expressing the thymidine gene are killed following treatment with GCV or a similar drug, whereas cells not expressing the thymidine kinase gene are unharmed by GCV treatment.

Preferably, the pancreatic cells being ablated express one or more transcription factors selected from the group consisting of BETA2, GATA4, E47 and PDX-1, and the promoter is a rat insulin promoter.

Another embodiment of the invention is directed to a method for selectively ablating a target in an individual using a suicide gene coupled to a promoter that is unique to the target. The method comprises transfecting the individual with an agent comprising a recombinant nucleic acid sequence comprising a thymidine kinase gene operatively linked or coupled to an insulin promoter, such as the rat insulin promoter, followed by treating or administering to the individual an effective amount of GCV, acyclovir, FIAU or 6-methoxypurine arabinoside in an amount sufficient to cause ablation of the target.

The cytotoxic effect may be enhanced by any mechanism that results in upregulating transcription of RIP-tk, such as, for example, addition of factors that upregulate transcription of RIP-tk or ablation of factors that inhibit transcription of RIP-tk. Factors that upregulate transcription of the rat insulin promoter include, for example, the BETA-2, GATA4, PDX-1 and E47 transcription factors. Factors that inhibit transcription of the rat insulin promoter include factors in the somatostatin signal transduction pathway, such as, for example, the somatostatin receptor subtype 5 (SSTR 5). In a preferred embodiment, the cytotoxic effect may be enhanced by co-transfecting RIP-tk with at least one of the rat insulin promoter transcription factors, BETA-2, GATA4, PDX-1 and E47.

In a preferred embodiment, liposomes are used for the delivery vehicle. Alternately, other delivery vehicles known to those of skill in the art, such as adenoviral vectors, may be used.

Preferably, the target comprises cells that express one or more transcription factors selected from the group consisting BETA2, GATA4, E47 and PDX-1. For example, the target may comprise cells of pancreatic origin, including, pancreatic cancer, insulin secreting tumors, PDX-1 positive pancreatic ductal carcinoma, β-cell tumors, insulinomas, β-cells, PANC-1 cells, CAPAN-1 cells, or NIT-1 cells.

Still another embodiment is directed to a method for treating a metabolic disease in an individual comprising administering to the individual an effective amount of an agent comprising a recombinant nucleic acid sequence. The nucleic acid sequence comprises a cytotoxic gene operatively linked to an insulin promoter. Preferably, the cytotoxic gene encodes thymidine kinase and the method further comprises the step of administering to the individual an agent selected from the group consisting of GCV, acyclovir, FIAU and 6-methoxypurine arabinoside. The metabolic disease may be hypoglycemia or hyperinsulinemia, such as hypoglycemia due to an insulin-secreting tumor or cell. In the latter case, the method preferably comprises the step of administering GCV to the individual in an amount effective to ablate the insulin-secreting tumor or cell.

The invention is also directed to compositions for selectively causing regression or ablation of a pancreatic cell. Such compositions preferably comprise a recombinant nucleic acid sequence comprising a target gene, such as the thymidine kinase gene, functionally or operatively linked to an insulin promoter. In a preferred embodiment, the promoter is a rat insulin promoter. The composition may be contained in a liposome delivery system, such as those described above. Alternatively, it may be contained in a viral vector. Cells which may be selectively targeted by the composition include the various cell lines disclosed herein, including, but not limited to, PDX-1 positive pancreatic ductal carcinoma cells, β-cell tumor cells, insulinoma cells, and β-cells.

The present invention is not limited to the RIP-tk construct disclosed herein. The present invention is also broadly directed to methods and constructs for targeting other tissues using unique promoters or genes specific to a particular tissue, to deliver a cytotoxic or suicide gene, such as tk, to the tissue to then kill the tumor. For example, in one embodiment of the invention, breast tissue may targeted by linking a suicide gene or other cytotoxin with an estrogen receptor promoter and/or a β casein promoter. In another embodiment, liver tissue may be targeted by using the α fetal protein promoter.

Still another embodiment of the invention is directed towards a method for the production of a protein in a cell. The method comprises delivering a nucleic acid molecule to the cell, wherein the nucleic acid molecule comprises an insulin promoter operatively linked to a structural nucleic acid sequence encoding the protein, and the cell comprises the PDX-1 transcription factor after delivery of the nucleic acid molecule. Alternatively, the cell may comprise the BETA-2 transcription factor after delivery of the nucleic acid molecule. The cell may comprise the PDX-2 transcription factor or the BETA-2 transcription factor before delivery of the nucleic acid molecule. The cell may naturally comprise the PDX-1 transcription factor or the BETA-2 transcription factor. The cell may generally be any type of cell, such as a pancreatic cell. When the cell is a pancreatic cell, the protein is preferably produced in the pancreatic cell at a higher concentration than in a non-pancreatic cell containing the nucleic acid molecule. The cell may be a pancreatic ductal carcinoma cell, a β-cell tumor cell, an insulinoma cell, or a β-cell, and preferably is a pancreatic ductal carcinoma cell. The cell may be PANC-1, CAPAN-1, or NIT-1 cell lines. The insulin promoter may generally be any insulin promoter, preferably is a rat insulin promoter, and more preferably is SEQ ID NO:1. Alternatively, the insulin promoter can be an effective fragment of SEQ ID NO:1. An effective fragment is a truncation of SEQ ID NO:1 which exhibits substantially the same transcription ability as does SEQ ID NO:1. The effective fragment preferably exhibits at least about 80%, 85%, 90%, 95%, 96%, 97%, 98%, 99%, and ideally 100% of the transcription ability of SEQ ID NO:1. The effective fragment is preferably at least about 50%, 60%, 70%, 80%, 90%, 95%, 96%, 97%, 98%, or 99% of the length of SEQ ID NO:1. Alternatively, the insulin promoter can be a promoter having a high level of percent sequence identity to SEQ ID NO: 1. The level of percent sequence identity is preferably at least about 80%, 85%, 90%, 95%, 96%, 97%, 98%, or 99% sequence identity as compared to SEQ ID NO:1. Percent sequence identity is determined by aligning the two sequences with a commercial software package such as CLUSTALW version 1.6 (Thompson, J. D., et al. *Nucleic Acids Res.* 22(22): 4673–4680 (1994)). The number of matches between the two aligned sequences is divided by 502 and multiplied by 100 in order to obtain a percent sequence identity. The cell may further comprise one or more transcription factors selected from the group consisting of the BETA2 transcription factor, the GATA4 transcription factor, and the E47 transcription factor. The cell may comprise both the PDX-1 transcription factor and the BETA2 transcription factor. The cell may comprise the PDX-1 transcription factor, the BETA2 transcription factor, and one or more transcription factors selected from the group consisting of the GATA4 transcription factor and the E47 transcription factor. The protein may generally be any protein, and preferably is thymidine kinase. The delivery step may comprise contacting the cell with a recombinant viral vector. Alternatively, the delivery step may comprise contacting the cell with an adenovirus. The molecule may further comprise a structural nucleic acid sequence encoding one or more transcription factors selected from the group consisting of the BETA2 transcription factor, the GATA4 transcription factor, the E47 transcription factor, and the PDX-1 transcription factor. The method may further comprise delivering to the cell one or more transcription factors selected from the group consisting of the BETA2 transcription factor, the GATA4 transcription factor, the E47 transcription factor, and the PDX-1 transcription factor. The method may further comprise delivering a second nucleic acid molecule to the cell, wherein the second nucleic acid molecule encodes one or more transcription factors selected from the group consisting of the BETA2 transcription factor, the GATA4 transcription factor, the E47 transcription factor, and the PDX-1 transcription factor. The method may further comprise delivering ganciclovir, acyclovir, FIAU, or 6-methoxypurine arabinoside to the cell after delivery of the nucleic acid molecule. Delivering ganciclovir, acyclovir, FIAU, or 6-methoxypurine arabinoside to the cell preferably ablates the cell.

An additional embodiment of the invention is directed towards a method for ablating cells in an individual comprising delivering an agent to the individual, wherein the agent comprises a nucleic acid molecule, and the nucleic acid molecule comprises an insulin promoter operatively linked to a structural nucleic acid sequence encoding a cytotoxic protein. The cytotoxic protein can generally be any cytotoxic protein, and preferably is thymidine kinase. The method may further comprise delivering ganciclovir, acyclovir, FIAU, or 6-methoxypurine arabinoside to the individual after delivery of the agent. The insulin promoter may generally be any insulin promoter, preferably is a rat insulin promoter, and more preferably is SEQ ID NO:1. Alternatively, the insulin promoter may be an effective fragment of SEQ ID NO:1. An effective fragment is a truncation of SEQ ID NO:1 which exhibits substantially the same transcription ability as does SEQ ID NO:1. The effective fragment preferably exhibits at least about 80%, 85%, 90%, 95%, 96%, 97%, 98%, 99%, and ideally 100% of the transcription ability of SEQ ID NO:1. The effective fragment is preferably at least about 50%, 60%, 70%, 80%, 90%, 95%, 96%, 97%, 98%, or 99% of the length of SEQ ID NO:1. Alternatively, the insulin promoter may be a promoter having a high level of percent sequence identity to SEQ ID NO:1. The level of percent sequence identity is preferably at least about 80%, 85%, 90%, 95%, 96%, 97%, 98%, or 99% sequence identity as compared to SEQ ID NO:1. The cells may further comprise one or more transcription factors selected from the group consisting of the BETA2 transcription factor, the GATA4 transcription factor, and the E47 transcription factor. The cells may comprise both the PDX-1 transcription factor and the BETA2 transcription factor. The cells may comprise the PDX-1 transcription factor, the BETA2 transcription factor, and one or more transcription factors selected from the group consisting of the GATA4 transcription factor and the E47 transcription factor. The molecule may further comprise a structural nucleic acid sequence encoding one or more transcription factors selected from the group consisting of the BETA2 transcription factor, the GATA4 transcription factor, the E47 transcription factor, and the PDX-1 transcription factor. The method may further comprise delivering to the cell one or more transcription factors selected from the group consisting of the BETA2 transcription factor, the GATA4 transcription factor, the E47 transcription factor, and the PDX-1 transcription factor. The method may further comprise delivering ganciclovir, acyclovir, FIAU, or 6-methoxypurine arabinoside to the cell after delivery of the nucleic acid molecule. Delivering ganciclovir, acyclovir, FIAU, or 6-methoxypurine arabinoside to the cell preferably ablates the cell. The cells may generally be any type of cells. The cells may be pancreatic cells. The cells may be insulin secreting cancer cells. The cells may be PDX-1 positive pancreatic ductal carcinoma cells, pancreatic ductal carcinoma cells, β-cell tumor cells, insulinoma cells, or β-cells. The cells may be PANC-1 cells, CAPAN-1 cells, or NIT-1 cells. The agent may comprise liposomes or adenoviral vectors. The individual is preferably a mammal, and more preferably is a human.

An additional embodiment of the invention is directed towards a method of treating a metabolic disease in an individual, comprising delivering an agent to the individual, wherein the agent comprises a nucleic acid molecule, and the nucleic acid molecule comprises an insulin promoter operatively linked to a structural nucleic acid sequence encoding a cytotoxic protein. The metabolic disease may generally be any metabolic disease, and preferably is hypoglycemia or hyperinsulinemia. The individual is preferably a mammal, and more preferably is a human. The cytotoxic protein may generally be any cytotoxic protein, and preferably is thymidine kinase. The method may further comprise delivering ganciclovir, acyclovir, FIAU, or 6-methoxypurine arabinoside to the individual after delivery of the agent. The insulin promoter may generally be any insulin promoter, preferably is a rat insulin promoter, and more preferably is SEQ ID NO:1. Alternatively, the insulin promoter may be an effective fragment of SEQ ID NO: 1. An effective fragment is a truncation of SEQ ID NO:1 which exhibits substantially the same transcription ability as does SEQ ID NO:1. The effective fragment preferably exhibits at least about 80%, 85%, 90%, 95%, 96%, 97%, 98%, 99%, and ideally 100% of the transcription ability of SEQ ID NO: 1. The effective fragment is preferably at least about 50%, 60%, 70%, 80%, 90%, 95%, 96%, 97%, 98%, or 99% of the length of SEQ ID NO:1. Alternatively, the insulin promoter may be a promoter having a high level of percent sequence identity to SEQ ID NO:1. The level of percent sequence identity is preferably at least about 80%, 85%, 90%, 95%, 96%, 97%, 98%, or 99% sequence identity as compared to SEQ ID NO:1. The metabolic disease may comprise an insulin-secreting tumor or an insulin-secreting cell.

A further embodiment of the invention is directed towards an isolated nucleic acid molecule comprising an insulin promoter operatively linked to a structural nucleic acid sequence encoding a cytotoxic protein. The cytotoxic protein may generally be any cytotoxic protein, and preferably is thymidine kinase. The insulin promoter may generally be any insulin promoter, preferably is a rat insulin promoter, and more preferably is SEQ ID NO:1. Alternatively, the insulin promoter may be an effective fragment of SEQ ID NO:1. An effective fragment is a truncation of SEQ ID NO:1 which exhibits substantially the same transcription ability as does SEQ ID NO:1. The effective fragment preferably exhibits at least about 80%, 85%, 90%, 95%, 96%, 97%, 98%, 99%, and ideally 100% of the transcription ability of SEQ ID NO:1. The effective fragment is preferably at least about 50%, 60%, 70%, 80%, 90%, 95%, 96%, 97%, 98%, or 99% of the length of SEQ ID NO:1. Alternatively, the insulin promoter may be a promoter having a high level of percent sequence identity to SEQ ID NO:1. The level of percent sequence identity is preferably at least about 80%, 85%, 90%, 95%, 96%, 97%, 98%, or 99% sequence identity as compared to SEQ ID NO:1. The nucleic acid molecule may comprise a viral vector.

An additional embodiment of the invention is directed towards a kit comprising an isolated nucleic acid molecule, wherein the isolated nucleic acid molecule comprises an insulin promoter operatively linked to a structural nucleic acid sequence encoding a cytotoxic protein. The isolated nucleic acid molecule may be any of the isolated nucleic acid molecules described herein. The nucleic acid molecule may be contained in a container. The kit may further comprise one or more agents selected from the group consisting of ganciclovir, acyclovir, FIAU, and 6-methoxypurine arabinoside. The kit may comprise ganciclovir. The agent may be contained in a second container. Alternatively, the nucleic acid molecule and the agent may be contained in the same container. The cytotoxic protein may generally be any cytotoxic protein, and preferably is thymidine kinase. The cytotoxic protein is preferably cytotoxic to mammals, and more preferably is cytotoxic to humans.

A further alternative embodiment of the invention is directed towards a method for increasing the secretion of insulin in an individual comprising reducing the concentration of somatostatin receptor. The reducing step may comprise adding an agent which knocks out the nucleic acid sequence encoding the somatostatin receptor. The agent may be a nucleic acid molecule. The reducing step may comprise adding an antibody to the individual which binds to the somatostatin receptor. The individual preferably is a mammal, and more preferably is a human. The somatostatin receptor preferably is somatostatin subtype receptor 5. The somatostatin receptor preferably is in the pancreas of the individual.

The following examples are offered to illustrate embodiments of the invention, and should not be viewed as limiting the scope of the invention.

EXAMPLES

Example 1

Demonstration of β-Cell Specific Cytotoxicity Using a Rat Insulin Promoter Thymidine Kinase Construct a. Materials and Methods, and Summary of Results 0.502 kb of RIP (SEQ ID NO:1) was ligated to the reporter gene lacZ and ligated to tk. These two genes were transfected into several cell lines to ascertain β-cell specific expression and β-cell specific cytotoxicity in vitro. RT/PCR and EMSA were performed on NIT-1 cell RNA and nuclear extract, respectively, to determine the transcription factors present and responsible for RIP activation in NIT-1 cells. A mouse β-cell adenoma model was created with NIT-1 cells. These mice were treated with the RIP-tk gene and both blood sugars and animal viability were monitored.

Only the beta (NIT-1) cells stained blue after X-gal staining ($p<0.05$, $n=16$) or had detectable levels of beta-galactosidase protein ($p<0.05$, $n=6$) in vitro. A significant decrease in cell survival was observed in NIT-1 cells transfected with RIP-tk, in vitro ($p<0.05$, $n=48$). Messenger RNA for both BETA2 and PDX-1 was found in NIT-1 cells and a super shift was observed for both BETA2 and PDX-1. NIT-1 cell tumors were successfully targeted with the RIPlacZ gene. Mice innoculated with NIT-1 cells developed clinically relevant tumors with hypoglycemia and death at sixty days post innoculation. The in vivo delivery of the RIP-tk gene in combination with GCV inhibited hypoglycemia and animal death ($n=30$, $p<0.05$).

b. Generation of RIPlacZ and RIP-tk Constructs

All restriction enzymes unless otherwise noted were from GIBCO-BRL, Bethesda, Md. The plasmid pD46.21 (provided by Dr. Franco DeMayo, Departments of Cell Biology and Pediatrics, Baylor College of Medicine), which contains a β-galactosidase gene with a polyadenylation signal and a nuclear localization signal, was digested with HindIII, blunt ended with Klenow, and digested with BamHI. RIP in Blue-Script KS+ (provided by Dr. Ming-Jer Tsai, Department of Cell Biology, Baylor College of Medicine) was isolated with SstII, blunt ended with T4 polymerase (Promega, Madison, Wis.), digested with BamHI and ligated into restriction endonuclease treated pD46.21 following the standard procedure. The construct was verified by digesting with NotI and identifying a 4.1 kb band.

The RIP-tk construction was generated in two steps. First the coding sequence of tk, 66 bp upstream from the ATG, was isolated from pMC1TK-6 (provided by Dr. Arthur Beaudet, Department of Cell Biology, Baylor College of Medicine) with NotI, blunt ended with Klenow, and digested with BamHI. The isolated tk gene was then ligated with growth hormone polyA (GhpA), in Blue-Script, which was digested with EcoRI, blunt ended with Klenow, and digested with BamHI. This ligation was verified with HindIII.

Thymidine kinase-GHpA in Blue-Script was further digested with BamHI and NotI and ligated with isolated 0.502 kb of RIP previously digested with BamHI and NotI. The construct was verified by digesting with BamHI and NotI and identifying a 0.5 kb band.

c. Transient Transfection of Genetic Constructs/transfection Efficiency

All cell lines were obtained from The Tissue Core Facility at Baylor College of Medicine and grown in their respective media as recommended by ATCC, Bethesda, Md. Cells were plated into six well dishes growing in logarithmic phase (60–80% confluent) twenty-four hours prior to transfection. All cells were transfected with 1 μg of DNA per well (RIPlacZ, RSVlacZ, RIP-tk, hollow vector, and MC1-tk). The DNA was mixed with 6 μl of Fugene (Boehringer Mannheim, Indianapolis, Ind.) in 94 μl of Dulbecco's modified Eagle's medium without serum (Gibco-BRL, Bethesda, Md). 100 μl of solution was added to each well by mixing gently.

The maximum transfection efficiency for NIT-1 cells in vitro was ten percent. This was demonstrated using both the RIPlacZ gene and the RSVlacZ gene. Despite this transfection efficiency a 26% decrease in cell survival was observed in NIT-1 cells transfected with the RIP-tk gene. This may be accounted for by the bystander effect. The bystander effect results from the transfer of viral thymidine kinase proteins into cells through gap junctions (Pope I M, et al., 33(7) *Eur J Cancer*. 1005–16 (1997)). This allows for cells that were not originally transfected with a viral tk gene to become susceptible to the cytotoxicity of GCV, thereby increasing the number of cells being killed.

d. Detection of β-Galactosidase Gene Expression, X-Gal Staining

NIT-1, CV-1 (monkey renal cell), F9 (mouse embryonic carcinoma cell), 3T3 (mouse fibroblast cell) and H411 (mouse lung cell) cells were transfected with either RIPlacZ or RSVlacZ (provided by Dr. Jeff Rosen, Department of Cell Biology, Baylor College of Medicine). RSVlacZ served as a positive control to ensure that all cells were sufficiently transfected. Thirty-six hours post transfection cells were stained with X-gal staining solution to detect for the presence of the beta-galactosidase protein. This was done by first washing the cells with cold PBS (twice) and fixing, them with 0.5% glutaraldehyde, for 5 minutes. Cells were then washed with cold PBS (twice), and a X-gal staining solution containing 1M Mg-Cl$_2$, 5M NaCl, 0.5M HEPES, pH 7.3, 30 mM potassium ferricyanide, 30 mM potassium ferrocyanide, and 2% X-gal solution was added. Cells were then incubated at 37° C. for 24 hrs to develop the color. An independent observer verified the presence of blue color. The experiment was repeated four times and a total of sixteen wells examined per cell type.

Only the β-cell line NIT-1 demonstrated blue color, after transfection with RIPlacZ ($n=16$, $p<0.05$). All cell lines transfected with RSVlacZ developed blue color after X-gal staining ensuring that all cell types were adequately transfected. The percentage of NIT-1 cells staining blue with the RSVlacZ construct equaled the percentage of blue staining cells with the RIPlacZ construct and was assumed to be the transfection efficiency for NIT-1 cells for this experiment.

e. Detection of β-Galactosidase Gene Expression, Using a Luminometer

NIT-1 and F9 cells transfected with either RIPlacZ or RSVlacZ were subjected to Beta-galactosidase Reporter Gene Assay (Tropix, Bedford, Mass.). The assay was carried out in triplicate. Protein levels were determined using Bradford's Protein assay (Sigma, St. Louis, Mo.). Results are represented in light units and adjusted for protein content.

Transfection of RIPlacZ resulted in a significant increase in beta-galactosidase protein levels in NIT-1 cells compared to F9 cells, $2.9 \times 10^5$ light units for NIT-1 cells and $1.2 \times 10^5$ light units for F9 cells (n=6, p<0.05). Both cell types demonstrated an equal amount of beta-galactosidase after transfection with RSVlacZ, $3.7 \times 10^5$ light units for NIT-1 cells and $3.5 \times 10^5$ light units for F9 cells (n=6, p=NS). This ensured that F9 cells were adequately transfected. Background light units were equal between cell types as well, $1.3 \times 10^5$ light units for NIT-1 cells and $1.4 \times 10^5$ light units for F9 cells (n=6, p=NS).

f. Ganciclovir Dose Response Curve for NIT-1 Cells in Culture

Dose response curves with GCV for untransfected NIT-1 and F9 (control) cells were performed prior to cytoxicity studies with genetic constructs. NIT-1 cells were plated into a ninety-six well plate at a density of 5,000 cells per well and treated with GCV (0.1 to 2.5 μg/ml) to determine a dose response curve to GCV alone. The cells were treated daily for five days and cell viability was ascertained with an MTS assay. GCV was found to be toxic to untransfected NIT-1 cells at much lower doses than has been reported in the literature for other cell types (FIG. 1A) (Al-Hendy A, et al., 43 *Gynecologic and Obstetric Investigation* 268–275 (1997); Eastham J, et al., 7 *Human Gene Therapy*. 515–523 (1996); Chen S-H, et al., 91 *Proc. Natl. Acad. Sci. USA* 3054–3057 (1994); Tong X, et al., 61 *Gynecologic Oncology* 175–179 (1996)). The GCV toxicity dose response curve for F9 cells resembled other cell lines (FIG. I B). Specifically, FIG. 1A shows the dose response curve for NIT-1 cells given GCV. The x-axis shows GCV in μg/ml. The y-axis shows percent cell survival. Note that at concentrations of GCV 0.25 μg/ml and higher a significant decrease in cell survival is observed, n=8, *p<0.05, Unpaired Student t-test. FIG. 15B shows the dose response curve for F9 cells given GCV. The x-axis shows GCV in μg/ml. The y-axis shows percent cell survival. F9 cell toxicity resembles that of other published cell lines, n=8, *p<0.05, unpaired Student t-test.

At GCV dosages greater than 0.25 μg/ml survival for untransfected NIT-1 cells significantly decreased (n=8, p<0.05) (FIG. 1A). Based on this data, it was determined that 0.20 μg/ml is the maximum dose of GCV one can use to treat NIT-1 cells in culture. This is believed to be related to the fastidious nature of NIT-1 cells in culture, because it is not reproducible in vivo.

g. Treatment of Transfected Cells With Ganciclovir

NIT-1 and F9 cells were transfected with either the RIP-tk gene or a hollow vector (v) (negative control). A group of untransfected cells (C) was used to control for the effect of GCV alone on cell death. As a positive control, F9 cells were transfected with a tk construct driven by a ubiquitous promoter (MC1-tk) to ensure that the F9 cells were being sufficiently transfected and susceptible to the cytotoxic effects of thymidine kinase. Twenty-four hours post transfection the cells were re-plated into ninety-six will plates at a density of 5,000 cells per well, and subjected to GCV treatment with a dose of 0.5 to 0.20 μg/ml of GCV. The media was refreshed daily. Cell viability was determined by using an MTS assay (Promega, Madison, Wis.) read at an absorbency of 490 nm. Percent cell death was calculated utilizing the following formula:

$$\frac{A - B}{A} \times 100$$

where A is the absorbency at 490 nm of transfected cells not treated with GCV and B is the absorbency at 490 nm of transfected cells treated with GCV. Percent cell survival was calculated by subtracting the percent cell death from one hundred.

In cells transfected with RIP-tk, only NIT-1 cells demonstrated a significant and GCV dose dependent decrease in cell survival; 17.7% and 26.8% for 0.15 μg/ml and 0.2 μg/ml of GCV, respectively.

Figure 2:
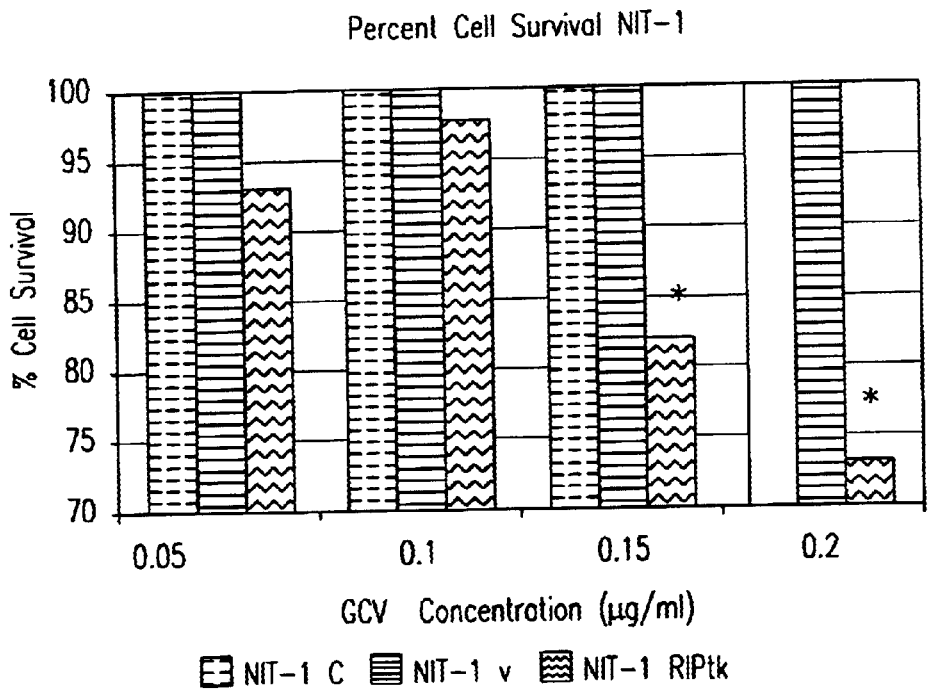
FIG. 2 is a bar graph showing the percent cell survival of NIT-1 cells transfected with nothing (C), a hollow vector (v), and RIP-tk with increasing levels of GCV.

Specifically, FIG. 2 is a bar graph which shows the percent cell survival of NIT-1 cells transfected with nothing (C), a hollow vector (v), and RIP-tk with increasing levels of GCV (μg/ml). As noted, only the RIP-tk gene demonstrated significant and GCV dose dependent decrease in NIT-1 cell survival, n=48, *p<0.05, ANOVA.

Figure 3:
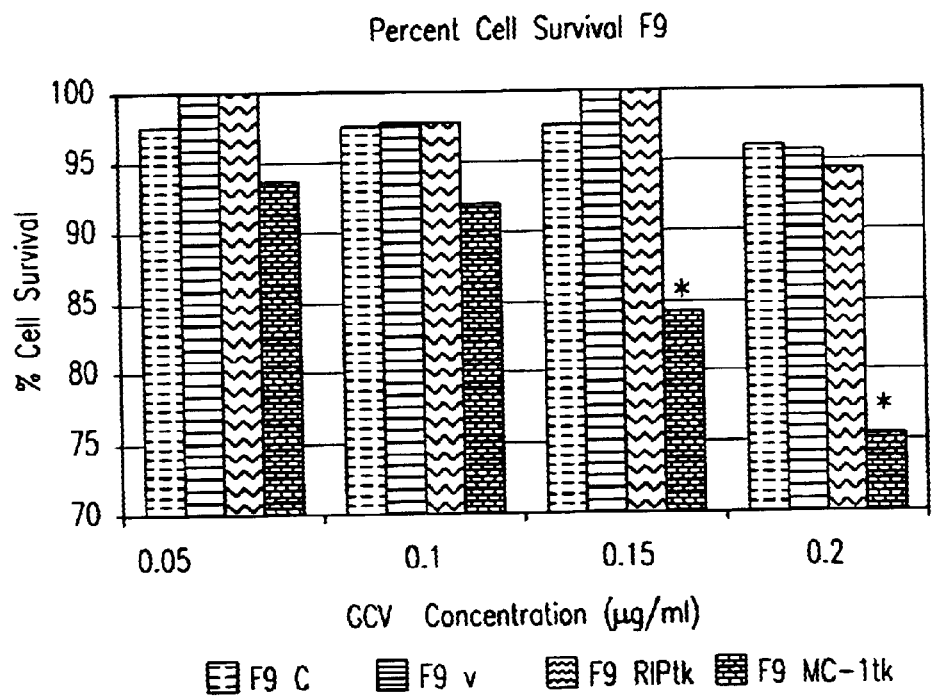
FIG. 3 is a bar graph showing the percent cell survival of F9 cells transfected with nothing (C), a hollow vector (v), RIP-tk, and MC1-tk with increasing levels of GCV.

F9 cells failed to show any significant decrease in cell survival with the RIP-tk gene following GCV treatment. F9 cells transfected with the positive control MC1-tk did demonstrate a significant decrease in cell survival; 15.5% and 24.3% for 0.15 μg/ml and 0.2 μg/ml of GCV, D respectively (FIG. 3). Neither cell type demonstrated any significant decrease in survival following transfection with a hollow vector (v) or with GCV treatment alone (C). Specifically, FIG. 3 is a bar graph which shows the percent cell survival of F9 cells transfected with nothing (C), a hollow vector (v), RIP-tk, and MC1-tk with increasing levels of GCV (μg/ml). As noted, no significant decrease in cell survival was demonstrated with the RIP-tk gene. A significant and GCV dose dependent decrease in F9 cell survival was demonstrated with the MC-1 tk ensuring that F9 cells were both adequately transfected and susceptible to the toxic effects of tk with GCV (n=48, *p<0.05, ANOVA).

h. NIT-1 mRNA Isolation and RT/PCR Analysis of Transcription Factors PDX-1 and BETA2

NIT-1 total RNA was extracted using RNAzol™ (Tel-Test, INC., Friendswood, Tex.). Briefly, cells were allowed to grow to confluence in large vented flasks. Media was removed and 5 ml of RNAzol™ was added. The cells were removed with the aid of a cell scraper and placed on ice for fifteen minutes. 500 μl of chloroform was added and the cells were spun for fifteen minutes at 10,000 rpm at 4° C. The aqueous phase was removed and mixed with an equal volume of isopropranol and placed at 4° C. for fifteen minutes and then spun for fifteen minutes at 15,000 rpm at 4° C. The pellet was then washed with 70% ethanol and re-spun at 15,000 rpm and allowed to dry.

Reverse transcriptase polymerase chain reaction (RT/PCR) was performed using SUPERSCRIPT™ Preamplification System for First Strand cDNA Synthesis kit (Gibco-BRL, Bethesda, Md.). Primers specific for mouse PDX-1 mRNA (forward 281–300 bps tgaacagtgaggagcagtac (SEQ ID NO:5) and reverse 870–889 bps ttttccacttcatgcgacgg (SEQ ID NO:6)) and primers specific for both human and mouse BETA2 (forward bps 944–964, cgccgagtttgaaaaaaatt (SEQ ID NO:7) and reverse bps 1227–1207, tttttccgacggaagacatt (SEQ ID NO:8)), (BETA2 primers were provided by Dr. Ming-Jer Tsai, Department of Cell Biology, Baylor College of Medicine) were used. Standard β-actin primers were used as controls. PCR program for all three primers was as following: 2 min 94° C., then thirty cycles of 1 min 94° C., 1 min 55° C., and 1 min 72° C. and 5 min 72° C. for finishing. 5 μd of the PCR reaction was run on gel electrophoresis. A 600 bp band identified a positive for PDX-1 and a 300 bp band identified a positive for BETA2. Thus, NIT-1 cells demonstrated a message for PDX-1 and BETA-2.

i. Nuclear Extracts and Electrophoretic Mobility-shift Assays (EMSA)

NIT-1 nuclear extracts were isolated as described elsewhere (Osaki T, et al., 54 *Cancer Research* 5258–5261 (1994)). Protein levels were determined using Bradford's Protein assay (Sigma, St. Louis, Mo.). A double-stranded oligodeoxynucleotide probe that contained both a BETA-2 site and a PDX-1 site within RIP (bp350–381 on RIP TTGGCCATCTGCTGATCCACCCTTAATGGGAC; SEQ ID NO:9) was labeled with $\alpha^{32}P$ dGTP by filling overhanging 5 ends with Superscript™ (Gibco-BRL, Bethesda, Md.). Binding reactions were performed with 2.5 μg of protein and 1 μl hot probe per lane on a 5% acrylamide gel with either nuclear extract alone or 100×cold wild type probe to assess protein binding. Supershift analysis for BETA-2 and PDX-1 binding activity was performed by the addition of 1 μl of anti BETA-2 antibody (provided by Dr. Ming-Jer Tsai, Department of Cell Biology, Baylor College of Medicine) and 1 μl of anti-N-terminal XIHbox8 antibody (provided by Dr. Christopher Wright, Department of Medicine, Vanderbilt School of Medicine), respectively.

Nuclear extract from NIT-1 cells demonstrated binding to the labeled oligonucleotide in RIP that contained both the BETA-2 and PDX-1 sites. Furthermore a supershift was observed with both the BETA-2 and PDX-1 antibodies.

j. Creation of an In Vivo Mouse β-Cell Adenoma Model

Twelve female ICR/scid mice, age 6–10 weeks underwent intraperitoneal injections of $5 \times 10^6$ NIT-1 cells as described (Tong X, et al., 61 *Gynecologic Oncology* 175–179 (1996)). An additional twelve female ICR/scid mice, age 6–10 weeks underwent an equal volume of PBS and were used as controls. To estimate tumor growth blood glucose was measured from the tail vein using a glucometer every other day. At animal death the mice underwent necrotopsies.

Figure 4:
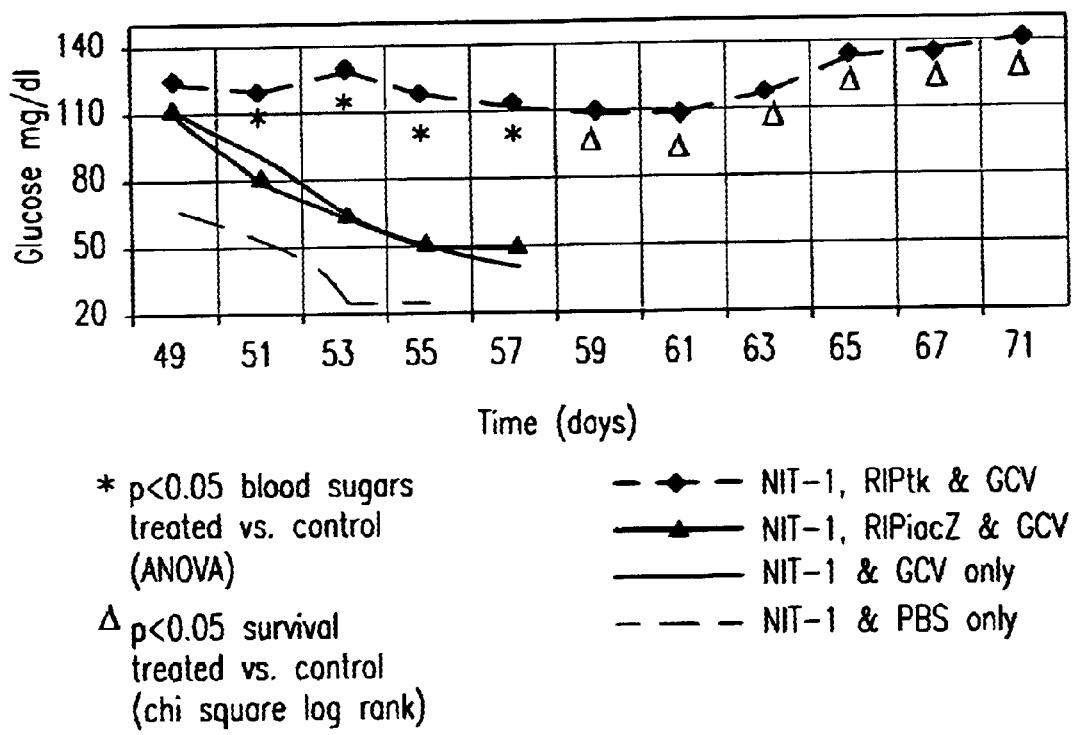
FIG. 4 is a graph showing blood sugars of ICR/scid mice injected EP with $5 \times 10^6$ NIT-1 cells, showing that NIT-1 cell tumors were successfully targeted with the RIPlacZ gene.

ICR/scid mice injected EP with $5 \times 10^6$ NIT-1 cells initially demonstrated no difference in blood sugars as compared to control mice. However, eight days prior to their death the mice demonstrated a rapid decline of their blood glucose levels and died (see FIG. 4). At autopsy, with the exception of one mouse, which had a small (<0.2 mm) subcutaneous tumor, no tumors were identified. NIT-1 cells added with PBS, GCV, or RIPlacZ and GCV led to the described rapid decline in blood glucose levels. Addition of NIT-1 cells with RIPtk and GCV prevented the decrease in blood glucose levels.

k. Treatment of β-Cell Adenomas (Insulinomas) In Vivo

Twenty-seven female ICR/scid mice, age 6–10 weeks old underwent intraperitoneal injections of $5 \times 10^6$ NIT-1 cells and nine female ICR/scid mice, age 6–10 weeks old underwent intraperitoneal injections of PBS. At day 31, the mice were randomized to receive either the RIP-tk gene, the RIPlacZ gene, or nothing. The RIP-lac-Z construct served both as a control and to localize gene expression. The genes were delivered via liposomes IP (liposomes provided by Dr. Nancy Smyth-Templeton Center for Gene Therapy and Department of Cell Biology, Baylor College of Medicine) and mixed as described (Smyth-Templeton N, et al., 15 *Nature Biotechnology* 647–652 (1997)). Six mice were randomized to receive the RIP-tk gene followed by seven days of GCV (40 mg/kg IP). Six mice were randomized to receive the RIP-lacZ gene followed by seven days of GVC (40 mg/kg IP). Six mice were randomized to receive PBS followed by seven days of GCV (40 mg/kg IP). Six mice that were inoculated with NIT-1 cells were randomized to receive seven days of PBS. Six mice which were inoculated with PBS were randomized to receive the RIP-tk gene followed by seven days of GCV (40 mg/kg IP).

Three mice that were inoculated with NIT-1 cells and three mice that were inoculated with PBS were randomized to receive the RIP-lacZ gene and then sacrificed thirty-six hours later. These mice had their tissues fixed including brain, heart, lung, liver, small bowel, spleen, kidneys, and pancreas in 5% glutaraldehyde for one hour, were stained with X-gal staining solution for twenty-four hours, and were sectioned and counter stained with nuclear fast red. Analysis of treatment and gene placement consisted of normalization of blood glucose values, inhibition of animal death, and presence of blue nuclei after X-gal staining.

NIT-1 cell tumors were successfully targeted with the RIPlacZ gene with tumors staining blue after fixation and X-gal staining. Five out of six experimental mice (received NIT-1 tumors, RIP-tk gene, and GCV) lived throughout the length of the experiment without any significant change in blood glucose values. The mouse that did demonstrate a decline of blood glucose levels and death had a technical problem in its administration of the RIP-tk gene; it was injected into the bladder. All of the other mice that received NIT-1 cells underwent a rapid decline in blood glucose values and died within sixty days of tumor innoculation (see FIG. 4).

ICR/scid mice injected with $5 \times 10^6$ NIT-1 cells exhibited an interesting response to increasing tumor burden. Despite the mice dying at different time points they all exhibited the same sequence of blood sugars prior to death; eight days prior to death they underwent a sequential decrease in blood sugars. This indicates there is a critical tumor burden that the mice can tolerate before their regulatory mechanisms are overcome and the mice die rapidly from hypoglycemia. The time it took to reach this critical tumor volume was not the same for each mouse and this can be explained, in part, by a learning curve associated with injecting the mice IP. Some mice probably had more tumor escape through the needle tract than others. In fact, one mouse had implantation of the tumor into the subcutaneous space. This proved to be beneficial because no tumors were discovered in the peritoneum of the other mice. In the subsequent in vivo experiment there were no subcutaneous tumors, and all of the mice began their decline in blood sugars and died within one week of each other, indicating that the technique had improved.

l. RIP Driven Expression in NIT-1 Cells In Vivo

In another murine hypoglycemic tumor model, $5 \times 10^6$ NIT-1 cells (or PBS) were injected intraperitoneally (IP) into ICR/scid mice (n=12 per group). A significant reduction of blood glucose values at 53±7 days and death at 60±7 days was observed in mice that received the NIT-1 cells. In a second experiment additional mice were randomized (n=6 per group) as follows: 1) NIT-1, RIP-tk and ganciclovir (GCV); 2) NIT-1, RIPlacZ and GCV; 3) NIT-1 and GCV only; and 4) NIT-1 and PBS only. GCV was given at 40 mg/kg IP BID for 7 days. RIP-tk and RIPlacZ genetic constructs were generated in the laboratory and were delivered IP 31 days post tumor injection by complexing the DNA with 20 mM of extruded DOTAP:cholesterol. Other mice injected with tumors and RIPlacZ had their tissues stained with X-gal. Blood glucose values, animal survival, and blue cells after X-gal staining were recorded. RT/PCR was done on NIT-1 RNA with primers specific for BETA2 and PDX-1. A band shift was performed by mixing NIT-1 nuclear extract with RIP and antibodies specific to PDX-1 and BETA2.

At animal death the insulinoma cells were identified by X-gal staining. RIP-tk in combination with GCV inhibited hypoglycemia and animal death in all mice (see FIG. 4). BETA2 and PDX-1 RNA was found in NIT-1 cells and both transcription factors demonstrated RIP binding with a super shift on the band shift.

m. Statistics

X-gal staining of cells used in this example (NIT-1, CV-1, F9, 3T3, and H411) were compared using both ANOVA and chi square test. The light units were adjusted for protein content and compared using an unpaired Student's t-test. Cell survival between different constructs and cell lines was compared with ANOVA. Mouse blood glucose levels were compared with ANOVA and animal survival was compared by chi square test. P<0.05 represented significance.

Example 2

Human Pancreatic Ductal Carcinoma Cells can be Targeted Using a RIP-tk Construct In Vitro a. Materials and Methods and Summary of Results 0.502 kb of RIP was ligated to the reporter gene lacZ and transfected into several human cell lines: human pancreatic ductal carcinoma cell lines (PANC-1, CAPAN-1, and MIA-1), lung carcinoma (A549), and breast carcinoma (T47D). X-gal staining and the detection of beta-galactosidase using a luminometer analyzed lacZ gene expression. RIP was ligated to tk and transfected into PANC-1, CAPAN-1, MIA-1, and A549 cells. Cell viability was compared after transfection with the RIP-tk genetic construct and daily treatment with of ganciclovir (GCV). RT/PCR was performed on PANC-1, CAPAN-1, and MIA-1 total RNA with primers specific for known insulin transcription factors PDX-1 and BETA2. EMSA was also performed on PANC-1 and CAPAN-1 nuclear extract using an antibody specific to PDX-1. A mutated RIPlacZ construct was created with one PDX-1 binding site changed. This construct was transfected into PANC-1 and CAPAN-1 cells and the amount of beta-galactosidase protein using a luminometer was assessed.

Only the pancreatic ductal carcinoma cells PANC-1 turned blue after X-gal staining (p<0.05, n=32 per cell type) and only PANC-1 and CAPAN-1 cells had detectable levels of beta-galactosidase protein (p<0.05, n=16). A significant increase in cell death was observed in PANC-1 and CAPAN-1 cells transfected with RIP-tk, while no significant increase in cell death was observed in A549 or MIA-1 cells transfected with RIP-tk (p<0.05, n=32). PANC-1 and CAPAN-1 cells contained RNA for PDX-1, but not for BETA2. MIA-1 cells did not contain RNA for either PDX-1 or BETA2. A super shift was observed with the PDX-1 antibody and nuclear extract from both PANC-1 and CAPAN-1. Decreased levels of beta-galactosidase protein was found in PANC-1 and CAPAN-1 cells transfected with the mutated RIPlacZ gene when compared to the wild type RIPlacZ gene (p<0.05, n=8). Finally, RIP was successfully used in a mouse model to drive expression of lacZ and tk in PANC-1 cells in vivo.

The data show that the RIP-tk gene is able to target and kill both PANC-1 and CAPAN-1 cells. The data also suggest that the transcription factor PDX-1, important in early embryonic pancreatic development, is responsible for both the activation and the targeting of the rat insulin promoter in PANC-1 and CAPAN-1 cells.

b. Generation of RIPlacZ and RIP-tk Constructs

All restriction enzymes unless otherwise noted were from GIBCO-BRL, Bethesda, Md. The plasmid pD46.21 (provided by Dr. Franco DeMayo, Departments of Cell Biology and Pediatrics, Baylor College of Medicine), which contains a β-galactosidase gene with a polyadenylation signal and a nuclear localization signal, was digested with HindIII, blunt ended with Klenow, and digested with BamHI. RIP in Blue-Script KS$^+$ (Stratagene, LA Jolla, Calif.) (provided by Dr. Ming-Jer Tsai, Department of Cell Biology, Baylor College of Medicine) was isolated with SstII, blunt ended with T4 polymerase (Promega, Madison, Wis.), digested with BamHI and ligated into restriction endonuclease treated pD46.21 following the standard procedure. The construct was verified by digesting with NotI and identifying a 4.1 kb band.

The RIP-tk construction was generated in two steps. First the coding sequence of tk, 66 bp upstream from the ATG, was isolated from pMC1TK-6 (provided by Dr. Arthur Beaudet, Department of Cell Biology, Baylor College of Medicine) with NotI, blunt ended with Klenow, and digested with BamHI. The isolated tk gene was then ligated with growth hormone polyA (GhpA), in Blue-Script, which was digested with EcoRI, blunt ended with Klenow, and digested with BamHI. This ligation was verified with HindIII.

Thymidine kinase-GHpA in Blue-Script was further digested with BamHI and NotI and ligated with isolated 0.502 kb of RIP previously digested with BamHI and NotI. The construct was verified by digesting with BamHI and NotI and identifying a 0.5 kb band.

c. Transient Transfection of Genetic Constructs

All PANC-1, CAPAN-1, MIA-1, A549 and T47D cell lines were obtained from American Tissue Core Facility (ATCC) (Bethesda, Md.). Cells were plated into six well dishes growing in logarithmic phase (60–80% confluent) twenty-four hours prior to transfection. All cells were transfected with 3 μg of DNA per well (RIPlacZ, RSVlacZ, RIP-tk, hollow vector, and Utk). The DNA was mixed with 6 μl of Fugene (Boehringer Mannheim, Indianapolis, Ind.) in 94 μl of Dulbecco's modified Eagle's medium without serum (Gibco-BRL, Bethesda, Md.). 100 μl of solution was added to each well by mixing gently.

d. Detection of β-Galactosidase Gene Expression, X-Gal Staining

PANC-1, CAPAN-1, MIA-1, A549, and T47D cells were transfected with either RIPlacZ or RSVlacZ (provided by Dr. Jeff Rosen, Department of Cell Biology, Baylor College of Medicine). RSVlacZ served as a positive control to ensure that all cells were sufficiently transfected. Thirty-six hours post transfection, cells were stained with X-gal staining solution by first washing the cells with cold PBS (twice) and fixing them with 0.5% glutaraldehyde, for 5 minutes. Cells were then washed again with cold PBS (twice), and a X-gal staining solution (containing 1M $MgCl_2$, 5M NaCl, 0.5M HEPES, pH 7.3, 30 mM potassium ferricyanide, and 2% X-gal solution) was added. Cells were then incubated at 37° C. for 6–24 hrs to develop the color.

As shown in Table 1, despite the variety of cell types, only the human pancreatic ductal carcinoma cell line PANC-1 demonstrated any significant blue color after transfection with RIPlacZ (n=32, p<0.05).

TABLE 1

| Cell Type | PANC-1 | CAPAN-1 | MIA-1 | A549 | T47D |
|---|---|---|---|---|---|
| RIPlacZ expression | 8%$^\Delta$ | 0% | 0% | 0% | <0.01% |
| RSVlacZ expression | 8%* | 0% | 8%$^T$ | 9%$^T$ | 6%$^T$ |

Table 1: Representation of lacZ expression after transfection with RIPlacZ or RSVlacZ and X-gal staining. Results verified by an independent observer and recorded as either positive or negative for blue color. Note that neither the RIPlacZ or the RSVlacZ demonstrated any staining for the CAPAN-1 cells.
N = 32 for each cell type,
$^\Delta$p < 0.05, PANC-1 with RIPlacZ vs MIA-1, A549, and T47D with RIPlacZ, ANOVA.
*p = NS, PANC-1 with RSVlacZ vs MIA-1, A549, and T47D with RSVlacZ, ANOVA.
$^T$p < 0.05, MIA-1, A549, and T47D with RSVlacZ vs MIA-1, A549, and T47D with RIPlacZ, chi square.

CAPAN-1 cells did not turn blue even with the RSVLacZ construct while all of the other cells transfected with RSV-lacZ developed blue color after X-gal staining ensuring that they were adequately transfected.

e. Detection of β-Galactosidase Gene Expression, Using a Luminonieter

PANC-1, CAPAN-1, MIA-1, and A549 cells, which were transfected with either RIPlacZ or RSVlacZ, were also subjected to Beta-galactosidase Reporter Gene Assay (Tropix, Bedford, Mass.). The assay was carried out in triplicate. Protein levels were determined using Bradford's Protein assay (Sigma, St. Louis, Mo.). Results were represented in light units and adjusted for protein content.

As shown in Table 2, transfection of RIPlacZ resulted in a significant increase in beta-galactosidase protein levels in both PANC-1 and CAPAN-1 cells compared to A549 and MIA cells.

TABLE 2

| Construct | PANC-1 | CAPAN-1 | A549 | MIA-1 |
|---|---|---|---|---|
| RSVlacZ | 9.7 × 10$^{5}$* | 9.1 × 10$^{5}$* | 9.2 × 10$^{5}$ | 9.5 × 10$^{5}$ |
| HV | 1.3 × 10$^{5}$* | 1.0 × 10$^{5}$* | 1.2 × 10$^{5}$ | 1.1 × 10$^{5}$ |
| Untransfected | 1.2 × 10$^{5}$* | 1.1 × 10$^{5}$* | 1.3 × 10$^{5}$ | 1.3 × 10$^{5}$ |
| RIPlacZ | 3.8 × 10$^{5\Delta}$ | 4.2 × 10$^{5\Delta}$ | 1.2 × 10$^{5}$ | 1.2 × 10$^{5}$ |

Table 2: Beta-galactosidase activity in PANC-1, CAPAN-1, A549, and MIA-1 cells thirty-six hours post-transfection with either RSVlacZ, a hollow vector (HV), nothing or RIPlacZ. Data represented in light units and adjusted for protein content.
n = 6,
$^\Delta$p < 0.05, ANOVA,
*p = NS.

All cell types demonstrated and equal amount of beta-galactosidase after transfection with RSVlacZ ensuring that both A549 and MIA-1 cells were adequately transfected. Background light units were also equal between cell types (Table 2).

f. Ganciclovir Dose Response Curve for Cells in Culture

PANC-1, CAPAN-1 MIA-1 and A549 cells were plated into a ninety-six well plate at a density of 5,000 cells per well and given between 0 to 500 μg/ml of GCV to determine a dose response curve to GCV alone. The cells were treated for five days and cell viability was ascertained with an MTS assay. Results were plotted on a graph as OD 490 nm vs. GCV concentration.

Figure 5A:
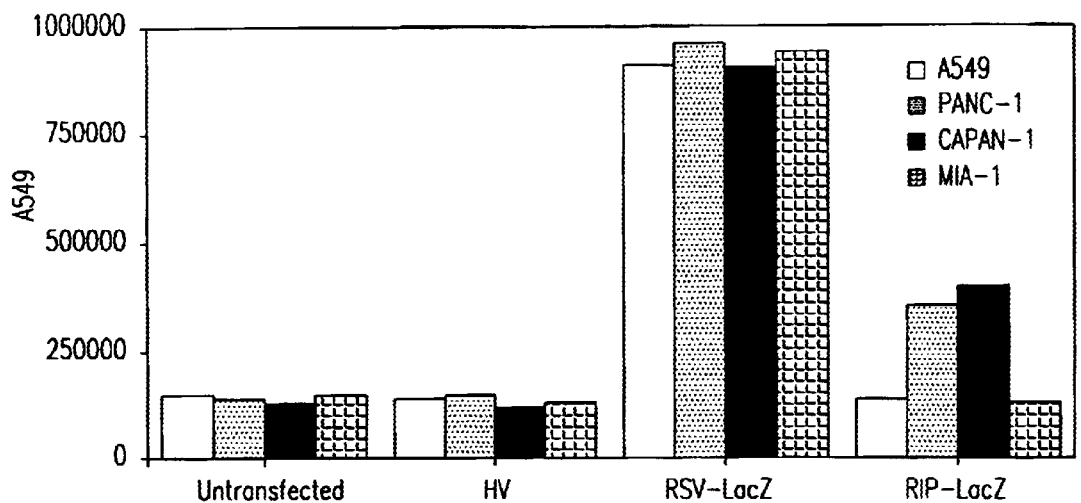
FIG. 5A is a dose response curve for PANC-1 cells given GCV.

PANC-1, CAPAN-1, A549, and MIA-1 cells were transfected with a control vector, RSV-LacZ, or RIP-LacZ plasmid for 36 hours. Cells were washed and collected. The β-galactosidase activity from each transfection was determined using a luminometer. Data was obtained in light units, and was corrected for protein content (FIG. 5A). The vertical axis is in light units per μg/ml protein. As shown in FIG. 5A, GCV dosages greater than 50 μg/ml significantly decreased untransfected PANC-1 and A549 cell OD 490 compared to cells that received no GCV (n=8, p<0.05) Specifically, FIG. 5A is a dose response curve for PANC-1 cells given GCV. Note that at concentrations of GCV greater than 50 μg/ml, a significant decrease in cell survival was observed, n=8, *p<0.05, unpaired Student t-test. This determined that 20 μg/ml is the maximum dose of GCV one can use to treat PANC-1 cells in culture, and was used for subsequent experiments.

Figure 5B:
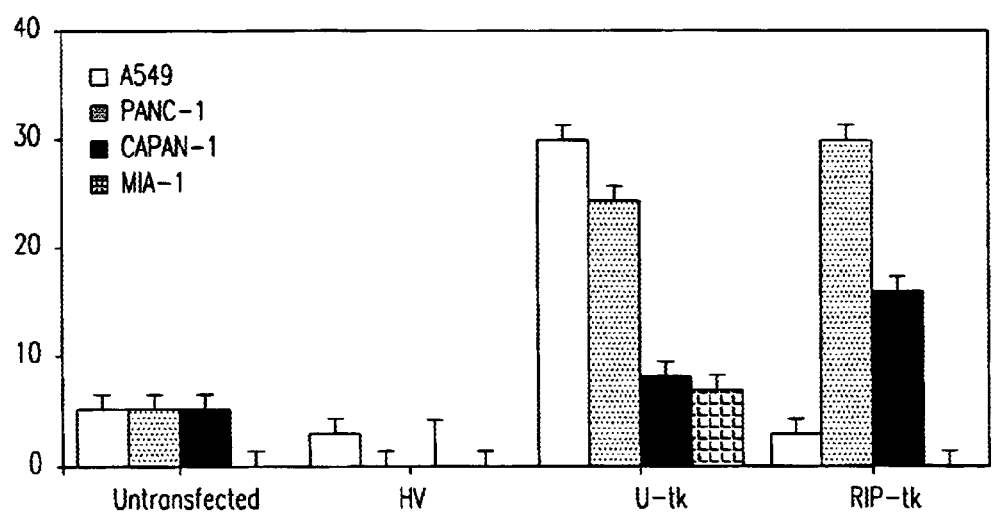
FIG. 5B is a dose response curve for CAPAN-1 cells given GCV.

PANC-1, CAPAN-1, A549, and MIA-1 cells were transfected with RIPtk, Utk (tk with a ubiquitous promoter), HV (hollow vector), or UT (untransformed) for 36 hours in order to assay cell death. All cells were treated for five days with either 15 or 20 μg/ml of GCV. Cell viability was determined by an MTS assay (Promega, Madison, Wis.). The data is shown in FIG. 5B. The vertical axis is percent cell death. As shown in FIG. 5B, GCV dosages greater than 20 μg/ml significantly decreased untransfected CAPAN-1 and MIA-1 cell OD 490 compared to cells that received no GCV (n=16, p<0.05). Specifically, FIG. 5B is a dose response curve for CAPAN-1 cells given GCV. Note that at concentrations of GCV greater than 20 μg/ml, a significant decrease in cell survival was observed, n=8, *p<0.05, unpaired Student t-test. This determined that 15 μg/ml is the maximum dose of GCV one can use to treat CAPAN-1 cells in culture, and was used for subsequent experiments.

g. Treatment of Transfected Cells With Ganciclovir

PANC-1, CAPAN-1, MIA-1 and A549 cells were transfected with either RIP-tk gene, a hollow vector control (HV), or with thymidine kinase construct that was driven by a ubiquitous promoter (Utk) (provided by Dr. Fanco DeMayo, Departments of Cell Biology and Pediatrics, Baylor College of Medicine). Twenty-four hours post transfection the cells were re-plated into ninety-six will plates at a density of 5,000 cells per well, and subjected to GCV treatment at a dose of 15–20 μg/ml. The media was refreshed daily. Cell viability was determined by using an MTS assay (Promega, Madison, Wis.) read at an absorbency of 490 nm. Percent cell death was calculated utilizing the following formula:

$$\frac{A - B}{A} \times 100$$

Where A is the absorbency at 490 nm of transfected cells not treated with GCV and B is the absorbency at 490 nm of transfected cells treated with GCV. Cell survival was calculated by subtracting the percent cell death from one hundred. Untransfected cells (UT) were also treated with ganciclovir to determine the effect of GCV alone on cell death.

As shown in Table 3, in cells transfected with the RIP-tk genetic construct both the PANC-1 and CAPAN-1 cells demonstrated a significant increase in cell death; 31±0.1% and 13±0.1% (Table 4). Both MIA-1 and A549 cells failed to show any significant increase in cell death with the RIP-tk gene.

TABLE 3

|  | RIPtk | Utk | HV | UT |
|---|---|---|---|---|
| PANC-1 | 31 ± 0.1^Δ* | 25 ± 0.3 | 0 ± 0.1 | 4 ± 0.1 |
| A549 | 2 ± 0.1 | 30 ± 0.1 | 2 ± 0.1 | 4 ± 0.1 |
| CAPAN-1 | 13 ± 0.1^TΛ | 8 ± 0.1 | 0 ± 0.3 | 4 ± 0.1 |
| MIA-1 | 0 ± 0.1 | 7 ± 0.1 | 0 ± 0.1 | 0 ± 0.1 |

Table 3: Percent cell death for PANC-1, CAPAN-1, A549, and MIA-1 cells transfected with RIP-tk, Utk (tk with a ubiquitous promoter), HV (hollow vector) and UT (untransfected). All cells were treated for five days with 20 μg/ml of GCV. Cell viability ascertained by an MTS assay (Promega, Madison, WI).
$^Δ$p < 0.05, PANC-1 with RIP-tk vs. A549 and MIA-1 with RIP-tk and PANC-1 with HV and UT.
*p = NS, PANC-1 with RIP-tk vs. PANC-1 with Utk and A549 with Utk.
$^T$p < 0.05, CAPAN-1 with RIP-tk vs. A5491 and MIA-1 with RIP-tk and CAPAN-1 with HV and UT.
$^Λ$p = NS, CAPAN-1 with RIP-tk vs. CAPAN-1 with Utk and MIA-1 with Utk.

None of the cell types demonstrated any significant increase in cell death following transfection with the negative controls, hollow vector (HV) or with GCV treatment alone (UT) (Table 3). All cell lines with the positive control Utk demonstrated a significant increase in cell death (Table 3). The data suggest that all cell types were sufficiently transfected and susceptible to the cytotoxic effects of tk followed by GCV.

h. RNA Isolation and RT/PCR Analysis of RIP Transcription Factors PDX-1 and BETA2

PANC-1, CAPAN-1, and MIA-1 total RNA was extracted using RNAzol™ (Tel-Test, INC., Friendswood, Tex.). Cells were grown to confluence in large vented flasks. Media was removed and 5 ml of RNAzol™ was added. Cells were removed and placed on ice for fifteen minutes. 500 μl of chloroform was added and the cells were spun for fifteen minutes at 10,000 rpm at 4° C. The aqueous phase was removed and mixed with an equal volume of isopropranol and placed at 4° C. for fifteen minutes and then spun for fifteen minutes at 15,000 rpm at 4° C. The pellet was then washed with 70% ethanol and re-spun at 15,000 rpm, and then dried.

Reverse transcriptase polymerase chain reaction (RT/PCR) was performed using SUPERSCRIPT™ Preamplification System for First Strand cDNA Synthesis kit (Gibco-BRL, Bethesda Md.). Primers specific for human PDX-1 RNA (forward bps 192–210, gggaacgccacacagtgcca (SEQ ID NO:10) and reverse bps 644–624, gtaccctttccgtcgacctg (SEQ ID NO:11) and primers specific for both human and mouse BETA2 RNA (forward bps 944–964, cgccgagtttgaaaaaaatt; SEQ ID NO:7, and reverse bps 1227–1207, tttttccgacggaagacatt; SEQ ID NO:8), (BETA2 primers were provided by Dr. Ming-Jer Tsai, Department of Cell Biology, Baylor College of Medicine) were used. Standard β-actin primers were used as controls. PCR program for all three primers was as following: 2 min 94° C.; then thirty cycles of 1 min 94° C., 1 min 55° C., and 1 min 72° C.; and 5 min 72° C. for finishing. 5 μl of the PCR reaction was run on gel electrophoresis. A 400 bp band identified a positive for PDX-1 and a 300 bp band identified a positive for BETA2. NIT-1 cell (mouse β-cell adenoma cell line) RNA was used as a positive control for the BETA2 primers.

Figure 5C:
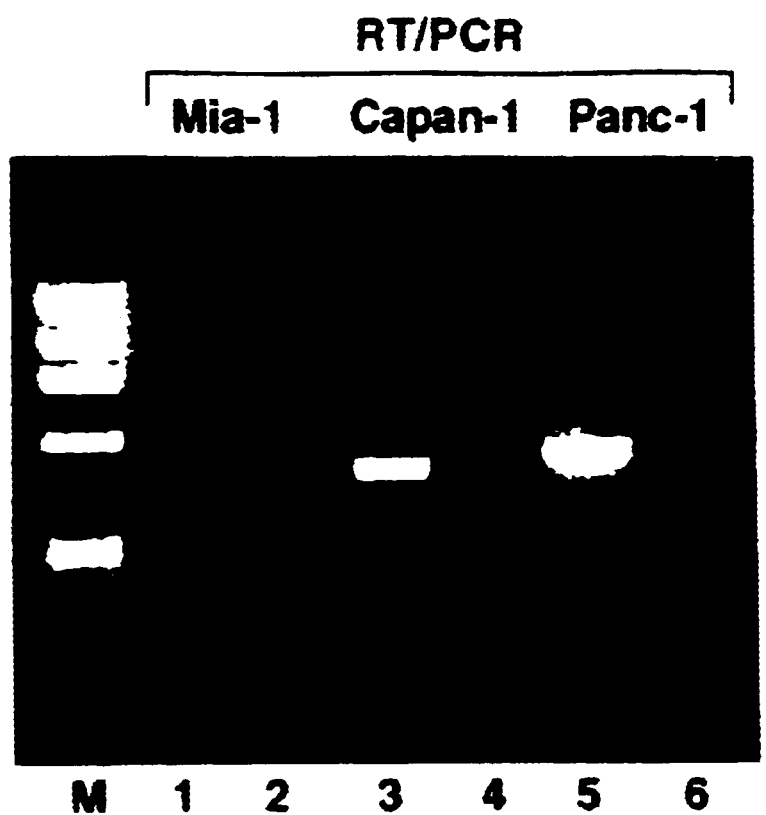
FIG. 5C is a gel electrophoresis for RT/PCR products of PANC-1, CAPAN-1 and MIA-1 RNA, with primers specific for PDX-1 and BETA2.

PDX-1 RNA was identified in PANC-1 and CAPAN-1 cells (FIG. 5C). BETA2 RNA was not found. BETA2 RNA was identified in a NIT-1 cell line control (FIG. 5C). MIA-1 cells contained no RNA for either PDX-1 or BETA2 (FIG. 5C). Specifically, FIG. 5C is a gel electrophoresis for RT/PCR products of PANC-1, CAPAN-1 and MIA-1 RNA with primers specific for PDX-1 (odd lanes) and BETA2 (even lanes).

i. Nuclear Extracts and Electrophoretic Mobility-shift Assays (EMSA)

Nuclear extracts were isolated as described by Olson et al. (Olson L, et al., 12(2) Mol. Endocrinol. 207–219 (1998)). Protein levels were determined using Bradford's Protein assay (Sigma, St. Louis, Mo.). A double-stranded oligodeoxynucleotide probe to the PDX-1 site within RIP (bp350–381 on RIP TTGGCCATCGTCtGATCCAACCCT-TAATGGGAC; SEQ ID NO:9) was labeled with $\alpha^{32}$P dGTP by filling overhanging 5 ends with Superscript™ (Gibco-BRL, Bethesda Md.) Binding reactions were performed with 1.5 μg of protein and 1 μl hot probe per lane on a 5% acrylamide gel with either nuclear extract alone, 100×cold wild type probe, or 100×cold mutated probe to assess protein binding (the mutated probe contained the same sequence of RIP as the wild type probe except the PDX-1 binding site was altered from CTTAAT (SEQ ID NO:4) to CTCCCC (SEQ ID NO:12)). Supershift analysis for PDX-1 binding activity was performed by the addition of 1 μl of anti-N-terminal XIHbox8 antibody (provided by Dr. Christopher Wright, Department of Medicine, Vanderbilt University School of Medicine).

Nuclear extract from PANC-1 and CAPAN-1 cells bound to the RIP primer containing a PDX-1 binding site. The binding was effectively inhibited by cold primer and not by cold mutated primer (same sequence of RIP with the PDX-1 binding site altered, CTTAAT (SEQ ID NO:4) to ATATAC (SEQ ID NO: 13)). A supershift was observed using the XIHbox8 antibody (FIGS. 6A and 6B).

Figure 6A:
FIG. 6A is an EMSA of PANC-1 nuclear extract mixed with $\alpha^{32}P$ dGTP labeled RIP primer containing a PDX-1 binding site (CTTAAT).
Figure 6B:
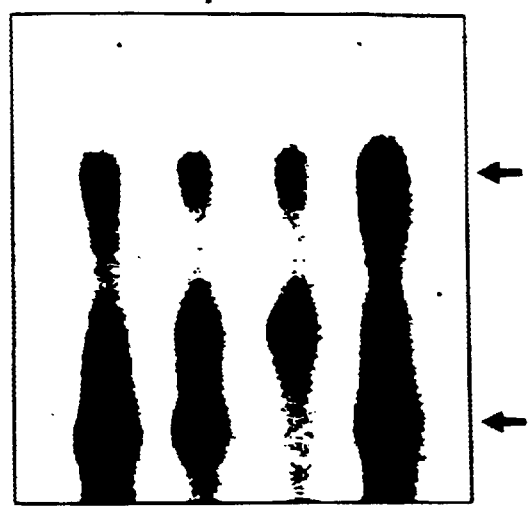
FIG. 6B is an EMSA of CAPAN-1 nuclear extract mixed with $\alpha^{32}$ p dGTP labeled RIP primer containing a PDX-1 binding site (CTAAT).

Results are shown in FIGS. 6A and 6B. Specifically, FIG. 6A is an EMSA of PANC-1 nuclear extract mixed with $\alpha^{32}$P dGTP labeled RIP primer containing a PDX-1 binding site (CTTAAT; SEQ ID NO:4). Lane 1 is nuclear extract with hot probe alone. Arrow denotes prominent band. Lane 2 is nuclear extract with hot probe and 100×competitor cold probe. Note that a band is no longer present. Lane 3 is nuclear extract with hot probe and 100×competitor cold mutated probe (PDX-1 site in RIP is mutated to ATATAC (SEQ ID NO:13). Note that a band is present. The mutated probe is unable to compete the hot probe off the nuclear extract. Lane 4 is nuclear extract with hot probe plus 1 μl of XIHbox8 antibody (specific for PDX-1). The arrow denotes the supershift.

FIG. 6B is an EMSA of CAPAN-1 nuclear extract mixed with $\alpha^{32}$P dGTP labeled RIP primer containing a PDX-1 binding site (CTTAAT; SEQ ID NO:4). Lane 1 is probe alone. Lane 2 is nuclear extract with hot probe alone. Arrow denotes prominent band. Lane 3 is nuclear extract with hot probe and 100×competitor cold probe. Note that a band is no longer present. Lane 4 is nuclear extract with hot probe plus 1 μl of XIHbox8 antibody (specific for PDX-1). The arrow denotes the supershift. Lane 5 is nuclear extract with hot probe and 100×competitor cold mutated probe (PDX-1 site in RIP is mutated to ATATAC; SEQ ID NO: 13). Note that a band is present. The mutated probe is unable to compete the hot probe off the nuclear extract.

j. Generation of Mutated RIPlacZ

Two oligonucleotides were designed to PCR amplify RIP and mutate the PDX-1 binding site found at 430. The sequence was mutated from CTTAAT to ATATAC The 5' oligonucleotide contained a HindIII binding site (sequence GAAAGCTTTCTGCTTTCCTTCTACCTC (SEQ ID NO: 14) and the 3' oligonucleotide contained a BglII restriction site (in bold, SEQ ID NO:15, sequence TCTAGAGCTTG-GACTTTGCTGTTTGTCCCGTATATGGTGGATCAG CAG). The restriction sites were added to facilitate construct formation. The PCR program was as following: 2 min 94°

3C.; then thirty cycles of 1 min 94° C., 1 min 55° C., and 1 min 72° C.; and 5 min 72° C. for finishing. 5 µl of the PCR reaction was run on gel electrophoresis. A sole 450 bp band identified the PCR product which was then ligated into a TA cloning vector (Invitrogen, Carlsbad, Calif.). The ligation was confirmed with EcoRI and the identification of a 450 bp band. Gene sequencing of the vector was performed (Core Sequencing Facility, Baylor College of Medicine).

To create the mutated RIP LacZ construct the mutated RIP was isolated from the TA cloning vector by digesting with BglII and HindIII. The isolated mutated RIP promoter was then ligated with the PD46.21 vector after it was digested with HindIII and BamHI. This ligation was verified with HindIII and ClaI with a 1.5 Kb band.

k. Comparison of Mutated RIPlacZ and Wild Type RIPlacZ

PANC-1 and CAPAN-1 cells were transfected with either the mutated RIPlacZ or the wild type RIPlacZ as described above. Thirty-six hours post transfected the cells were subjected to Beta-galactosidase Reporter Gene Assay (Tropix, Bedford, Mass.). The assay was carried out in triplicate. Protein levels were determined using Bradford's Protein assay (Sigma, St. Louis, Mo.). Results were represented in light units and adjusted for protein content.

As shown in Table 4, transfection of wild type RIPlacZ resulted in a significant increase in beta-galactosidase protein levels in both PANC-1 and CAPAN-1 cells as compared to the mutated RIPlacZ.

TABLE 4

| Construct | PANC-1 | CAPAN-1 |
|---|---|---|
| RIPlacZ | $1.0 \times 10^{5}$* | $1.4 \times 10^{5\Delta}$ |
| mRIPlacZ | $2.5 \times 10^{4}$ | $4.8 \times 10^{4}$ |

Table 4: Beta-galactosidase activity in PANC-1 and CAPAN-1 cells thirty-six hours post-transfection with either RIPlacZ or a mutated RIPlacZ (mRIPlacZ). Data represented in light units and adjusted for protein content (n = 8)
*$p < 0.05$, PANC-1 RIPlacZ vs PANC-1 mRIPlacZ, chi square.
$\Delta p < 0.05$, CAPAN-1 RIPlacZ vs CAPAN-1 mRIPlacZ, unpaired Student's t-test.

l. Treatment of Human Ductal Pancreatic Adenocarcinoma Tumors In Vivo

Female ICR/scid mice, age 6–10 weeks old underwent intraperitoneal (ip) injections of $5 \times 10^{5}$ PANC-1 cells or the negative control PBS as described (Schwartz R E, et al., 126(3) *Surgery* 562–567 (1999)). At day 21 the mice were randomized to receive the RIP-tk gene (n=9), the RIPlacZ gene (n=9), or PBS (n=6), followed by 7 days of GCV (40 mg/kg ip). Six mice received seven days of PBS IP. Genes complexed with 20 mM extruded DOTAP:cholesterol were delivered IP for in vivo gene delivery (Smyth-Templeton N, et al., 15 *Nature Biotechnology* 647–652 (1997)).

Three additional mice inoculated with PANC-1 cells received the RIPlacZ gene and were sacrificed thirty-six hours later. Brain, heart, lung, liver, small bowel, spleen, kidney, and pancreas were fixed in 5% glutaraldehyde for one hour, stained with X-gal staining solution for twenty-four hours, and then counterstained with nuclear fast red. Analysis of treatment and gene placement consisted of size of the tumor and presence of blue color after X-gal staining.

Twenty-one days post tumor the mice were randomized (n=6 per group) as follows: 1) PANC-1, RIP-tk and GCV; 2) PANC-1, RIPlacZ and GCV; 3) PANC-1 and GCV only; and 4) PANC-1 and PBS only. GCV was given at 40 mg/kg IP BID for 7 days to activate the tk. Additional injected mice with tumors (n=3) received RIPlacZ and their tissues were fixed and stained with X-gal. Study endpoints consisted of monitoring tumor size and the presence of blue cells after X-gal staining.

Figure 8:
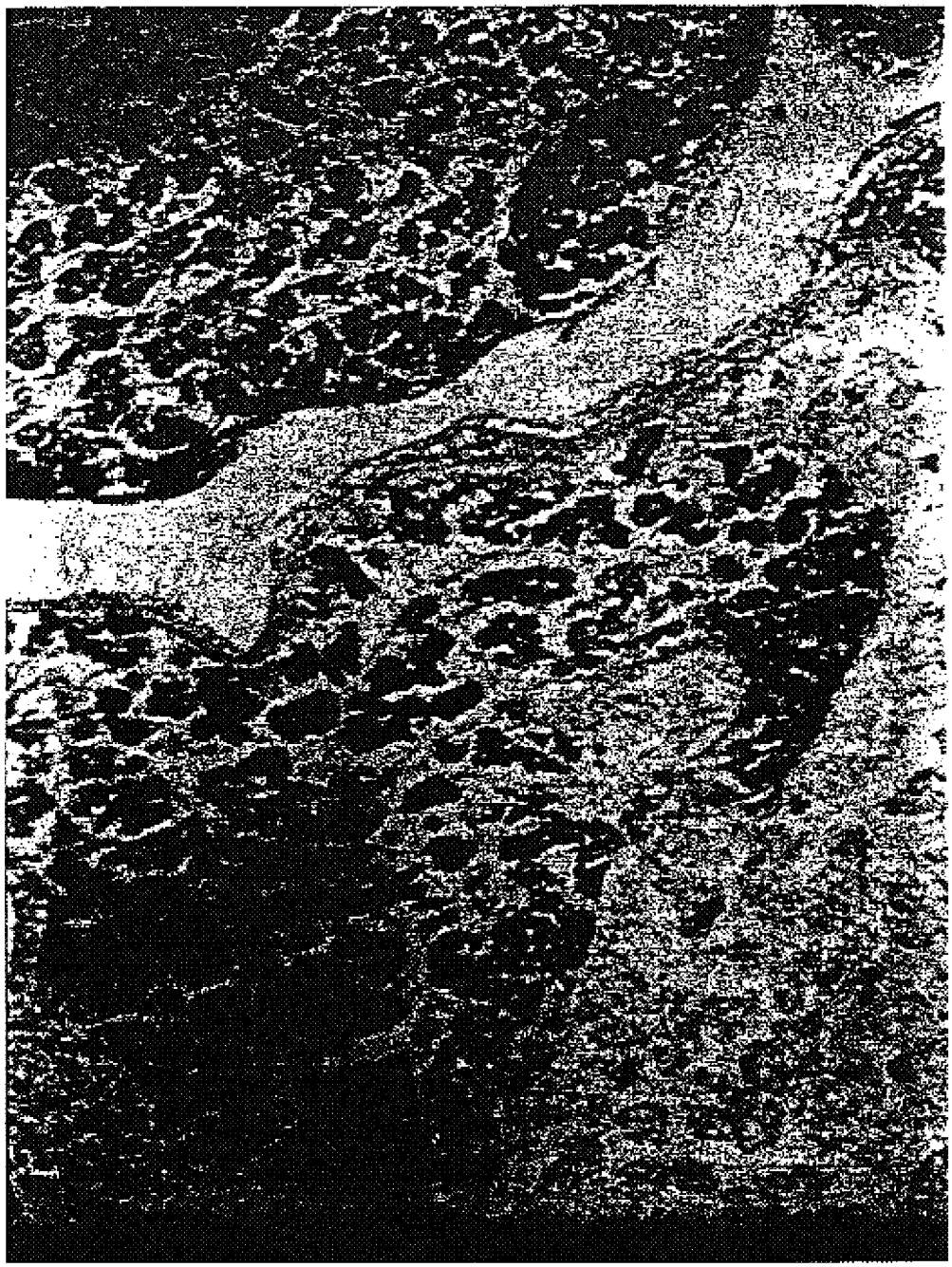
FIG. 8 is a photograph of stained cells demonstrating the expression of RIPlacZ in vivo in PANC-1 cells.

Results are shown in FIG. 8. FIG. 8 is a photograph of X-gal stained PANC-1 cells. PANC-1 cells were effectively targeted with the RIPlacZ gene in vivo; only the PANC-1 cells stained blue. The in vivo delivery of RIP-tk in combination with GCV resulted in a significant decrease in tumor burden in mice; the combination killed all PANC-1 tumors in eight of nine mice ($p<0.05$ compared to all other groups, ANOVA). Mice that received PANC-1 cells and treated with RIPlacZ (the vector control) and mice treated with only GCV developed large peri-pancreatic intraperitoneal tumors.

m. Statistics

All cells used in the experiment were compared using both ANOVA and chi square after X-gal staining. The light units were adjusted for protein content and compared using an unpaired Student's t-test. Cell survival was compared between different constructs and cell lines with ANOVA. Tumor sizes were compared using ANOVA. $P<0.05$ represented significance.

Example 3

Human Ductal Pancreatic Adenocarcinoma Cells That Express PDX-1 can be Targeted With a RIP-tk Gene RIPlacZ was created and transfected into CAPAN-1 (C-1) and MIA-1 (M-1) cell lines. RIP-tk was created and transfected into C-1 and M-1 cell lines. Tk driven by a ubiquitous promoter (Utk), a hollow vector (HV) and untransfected cells (UT) were used as controls. Cells were treated for five days with 15 µg/ml of ganciclovir and cell viability was assessed during a MTS assay. RT/PCR was performed on C-1 and M-1 RNA with primers specific for PDX-1 and BETA2. Nuclear extract from C-1 cells was subjected to a gel shift assay with an antibody to PDX-1. A PDX-1 binding site on RIP was mutated (mRIP) with PCR and a mRIPlacZ construct was created and transfected in C-1 cells. Results are shown in Table 5.

TABLE 5

| | Results: LacZ expression (LU) | | | Percent Cell Death | | | |
|---|---|---|---|---|---|---|---|
| | RIPZ | RSVZ | mRIPZ | RIPtk | Utk | HV | UT |
| C-1 | $4.2 \times 10^{5\Delta}$ | $9.1 \times 10^{5}$ | $1.4 \times 10^{5T}$ | $13 \pm .1$* | $8 \pm .1$ | $0 \pm .1$ | $4 \pm .1$ |
| M-1 | $1.2 \times 10^{5}$ | $0.5 \times 10^{5}$ | | $0 \pm .1$ | $7 \pm .1$ | $0 \pm .1$ | $0 \pm .1$ |

Table 5:
$\Delta p < 0.05$ C-1 RIPlacZ vs. M-1 PIPlaxZ, and $^{T}p < 0.05$ C-1 mRIPlacZ vs. C-1 RIPlaxZ, students t-test.
*$p < 0.05$ C-1 RIP-tk vs. M-1 RIP-tk and negative controls, ANOVA.

Neither cell type contained RNA for BETA 2, however C-1 cells contained RNA for PDX-1. The nuclear extract of C-1 cells bound to the PDX-1 sequence of RIP (CTTAAT) and a super shift was observed with the PDX-1 antibody.

The data confirm that RIP can drive the expression of a gene in human PDA cells. Additionally, the transcription factor PDX-1 is useful for promoter activation in human PDA cells.

Example 4

Selective Human Pancreatic Cancer Targeting Using an RIP-tk Construct (In Vitro Data)

This example further demonstrates that a human pancreatic ductal carcinoma cell line (PANC-1) may be selectively targeted using the rat insulin promoter (RIP) and that PANC-1 cytotoxicity may be induced using RIP with the thymidine kinase gene (tk).

0.502 kb of RIP was ligated to lacZ and transfected into human cancer cell lines: PANC-1, lung (A549), and breast (T47D), in vitro. Analysis of lacZ gene expression was by X-gal staining. RIP was also ligated to tk (RIP-tk) and transfected into PANC-1 and A549 cells. Untransfected cells (UT) and a hollow vector (HV) served as negative controls, while tk under the control of a ubiquitous promoter (M-tk) served as a positive control. Cells were treated daily with ganciclovir (GCV). Viability was measured on day six using an MTS assay. Results are shown in Table 6.

TABLE 6

| DATA: | | Percent Cell Death | | | |
|---|---|---|---|---|---|
| Cell | LacZ % | RIP-tk | M-tk | HV | UT |
| PANC-1 | 30 | 31 ± .1$^\Delta$ | 25 ± 3 | 0 ± .1 | 4 ± .1 |
| A549 | 0 | 2 ± .1 | 30 ± .1 | 2 ± .1 | 4 ± .1 |
| T47D | <1 | | | | |

Table 6:
*p <0.05,
$^\Delta$p < 0.0001 compared to PANC-1 (HV & UT) and A549 (RIP-tk, HV, & UT),
p = NS compared to M-tk for both cell lines, ANOVA (n = 32).

The resulting data confirm that RIP can drive the expression of a gene in human pancreatic ductal carcinoma (PANC-1) cells. The RIP-tk gene resulted in PANC-1 specific cytotoxicity as effective as M-tk. Thus, it can be concluded that PANC-1 can be targeted with RIP.

Example 5

Cell Specific Cytotoxicity Using RIP-tk Construct (In Vitro Data)

This example demonstrates the use of the rat insulin promoter (RIP) will result in the β-cell specific expression of a transfected gene and that one can induce β-cell specific cytotoxicity using RIP with the thymidine kinase gene (tk).

0.502 kb of RIP was ligated to the reporter gene lac-Z and tranfected into several cell lines: insulinoma (NIT-1), embryonic carcinoma (F9), fibroblast (3T3), and lung (H441) cells in vitro. X-gal staining analyzed the lac-Z gene where blue nuclei represented cellular expression. RIP was ligated to tk and transfected into NIT-1 and F9 cells. A hollow vector (v) and tk under the control of a ubiquitous promoter (MC-1tk) were used as negative and positive controls, respectively. The cells were treated daily with ganciclovir (GCV). Cell viability was ascertained on day six using an MTS assay. Results are shown in Table 7.

TABLE 7

| Results: | NIT-1 | F9 | 3T3 | H441 |
|---|---|---|---|---|
| Lac Z Expression | ++++ | – | – | – | n = 16 per cell type

Figure 9:
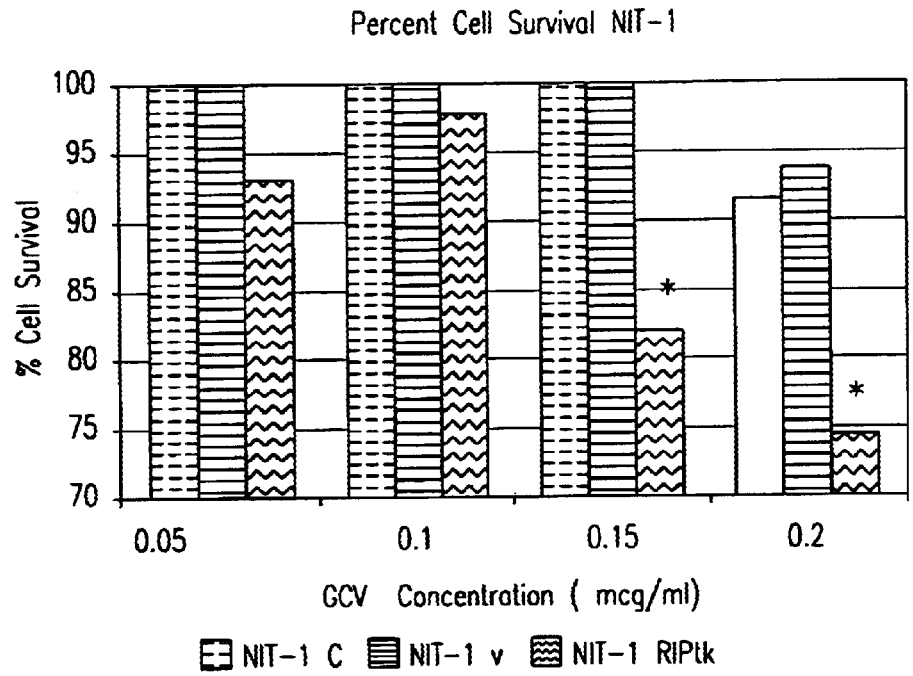
FIG. 9 contains two bar graphs depicting the cell survival percentages of NIT-1 (left) and F9 (right) cell lines following transfection and GCV treatment.
Figure 9:
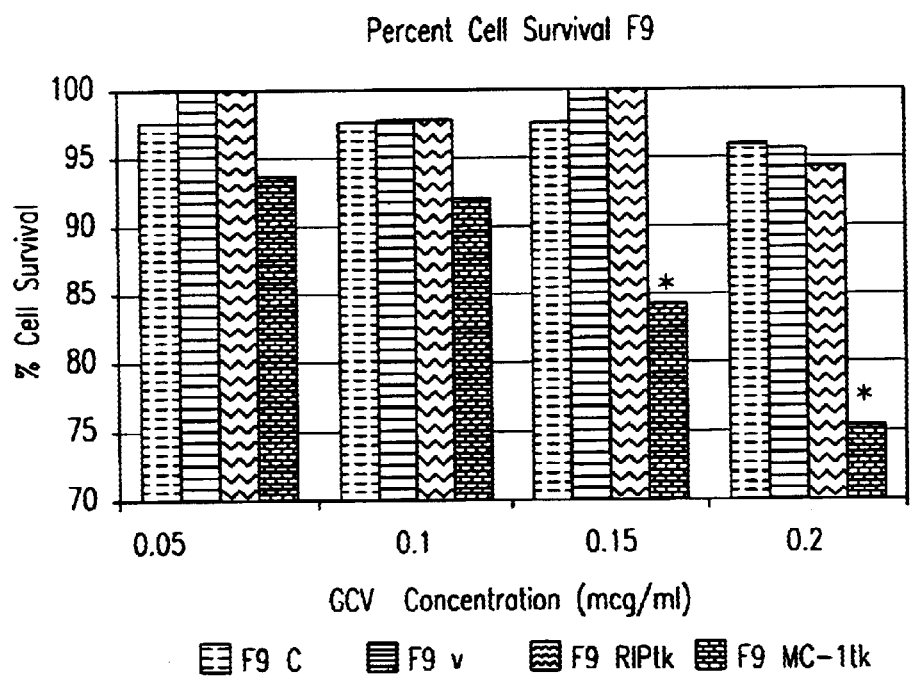

The bar graphs in FIG. 9 depict the cell survival percentages of NIT-1 and F9 cell lines following transfection and GCV treatment. The cells were transected with vectors encoding either RIP-tk (test), tk under the control of a ubiquitous promoter as a positive control (MC-1-tk), and tk in a hollow vector as a negative control (v), followed by treatment with GCV in the indicated concentration. (*p<0.05 via student t-test, n=48 per construct.)

The data indicates that the RIP is a β-cell specific promoter. A β-cell specific and GCV dose dependent decrease in NIT-1 cell survival was demonstrated with the RIP-tk gene. F9 cell death was shown using the MC-1tk gene at similar doses of GCV, but not with the RIP-tk gene indicating that β-cell targeted cell death can be accomplished by the tissue specific expression of tk by RIP.

Example 6

NIT Specific Killing With RIP-tk (In Vitro Data)

This is another example of NIT targeted cytotoxicity in vitro.

Two genetic constructs were created, RIP-lacZ and RIP-tk. The RIP-lacZ construct was delivered into NIT-1 cells and control cell lines. Only NIT-1 cells stained blue following X-gal staining, demonstrating NIT-1 specificity of RIP. Secondly, NIT-1 cells and control cells were transfected with RIP-tk construct, then treated with GCV. A highly significant ablation of only NIT-1 cells was achieved, demonstrating the NIT-1 specific killing effect of RIP-tk (Tirone et al., *Annals of Surgery*, in press).

Using RNA isolated from NIT-1 cells, the presence of the RIP transcription factor, BETA2, was demonstrated using RT-PCR. This observation supports the finding that the transcription factor BETA2 regulates the effect of RIP-tk in an insulinoma cell line.

Example 7

Enhancement of the Cytotoxic Effect of RIP-tk by RIP Transcriptional Factors BETA2, GATA4, and E47

BETA2 forms heterodimers with E47 and GATA4 and enhances RIP driven gene expression in β-cells (German M, et al., 75 *J Mol Med* 327–340 (1997)). The cytotoxic effect of RIP transcription factors BETA2, PDX-1, GATA4, and E47 in NIT-1 cells is assessed by co-transfecting these transcription factors with either RIP-tk or RIP-luciferase genetic constructs. Both cytotoxicity and luciferase activity is quantified.

Example 8

Alterations in Insulin Secretion in the SSTR5 Knock Out Mouse Using Isolated Perfused Mouse Pancreas Model SSTR-5 knock out (KO) mice 3-months-old (n=6), SSTR-5(somatostatin subtype receptor 5) KO mice 12-months-old (n=8), and age matched wild type (wt) controls (n=6 and n=8, respectively) were screened by Southern blots to determine their genotype. KO and wt mice 3 and 12 months old (n=4 per group) underwent histological examination of islets by an independent pathologist. Pancreata were isolated as described elsewhere with the exception that all pancreata remained in situ throughout their perfusion. (Lenzen S, 235(4) *Am. J. Physiol.* E391–E3400 (1979)). Single pass perfusion of isolated pancreata was performed using a Krebs buffer equilibrated with 95% $O_2$/5% $CO_2$ containing 70 mg % glucose for five minutes (basal) and 300 mg % glucose for an addition twenty-six minutes (stimulated). Basal insulin secretion, and glucose stimulated first and second phase insulin secretion were compared by calculating the area under the secretion vs. time curve utilizing the trapezoidal rule. (Chiou W L, 6(6) *J of Pharmacokinet and Biopharm* 539–546 (1978)). Insulin was measured in duplicate using, ELISA presented as mean±SEM in pg/ml. Statistical analysis was by ANOVA.

Histological sections of islets suggest there is no difference in islet cell morphology between 3-month-old KO and 3-month-old wt mice or 12-month-old KO and 12-month-old wt mice. There were no differences in weight between KO and aged match controls. There were no differences in basal insulin secretion between any of the mice. Additionally, glucose stimulation caused in a significant increase in insulin secretion compared to basal in all mice. Three-month-old KO mice demonstrated a blunted first phase that was significant compared to all other mice (Table 8 and FIG. 7). Twelve-month-old KO mice demonstrated a significant augmentation of both first phase and second phase compared to all other groups Results are shown in Table 8 and FIG. 7.

TABLE 8

|  | KO 3 mo | WT 3 mo | KO 12 mo | WT 12 mo |
| --- | --- | --- | --- | --- |
| Basal | 254 ± 9 | 279 ± 5 | 301 ± 11 | 266 ± 10 |
| 1st Phase | 248 ± 10*♦ | 318 ± 7♦ | 590 ± 17^Δ♦ | 417 ± 19♦ |
| 2nd Phase | 435 ± 9♦ | 457 ± 9♦ | 767 ± 18+♦ | 417 ± 9♦ |

Table 8: Average insulin levels in pg/ml. Basal insulin levels across all groups were similar (p = NS).
♦All mice experienced significant glucose stimulated insulin secretion compared to basal levels, $p < 0.05$.
*Three-month-old KO mice demonstrated a blunted first phase compared to all other groups, $p < 0.05$.
^ΔTwelve month-old KO mice demonstrated an increased first phase compared to all other groups, $p < 0.05$.
+Twelve month KO mice demonstrated an increased second phase compared to all other groups, $p < 0.05$.

Figure 7:
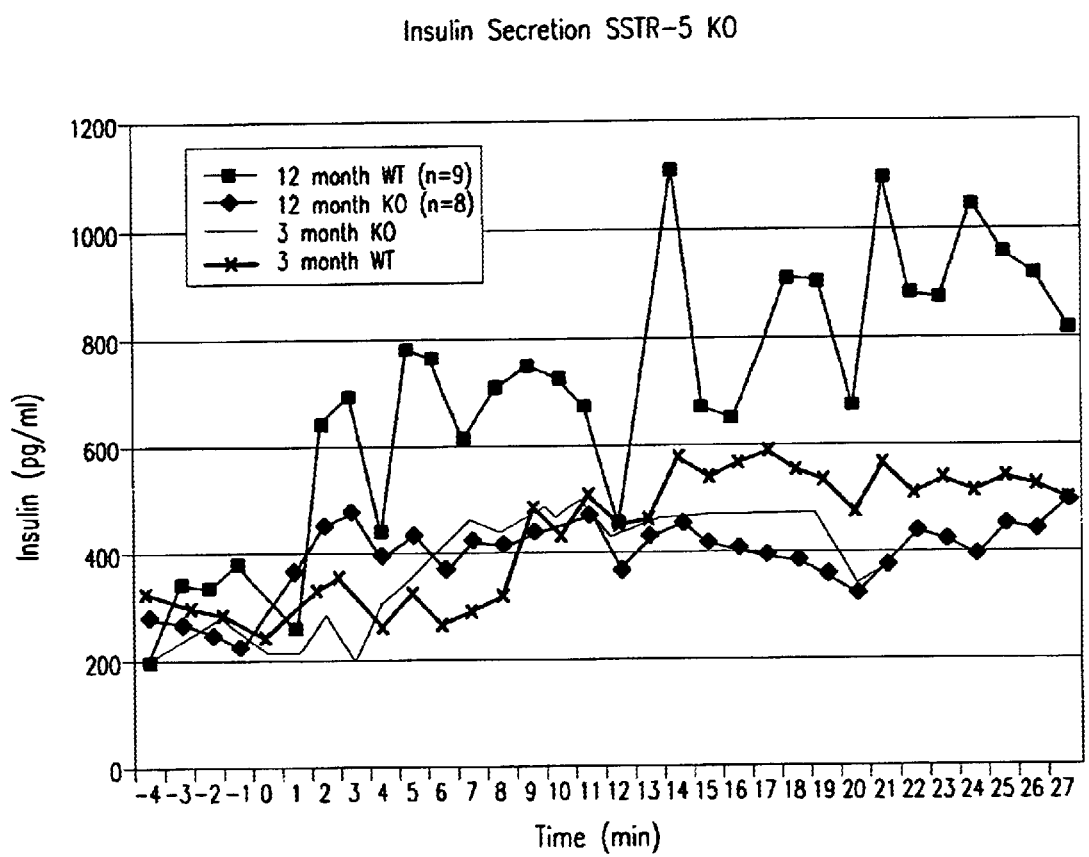
FIG. 7 is a glucose stimulated insulin versus time curve for 3-month-old and 12-month-old KO and wt mice.

FIG. 7 is a glucose stimulated insulin versus time curve for 3-month-old and 12-month-old SSTR-5 KO and wt mice. Glucose stimulation with 300 mg % glucose started at time zero. There was no significant difference in basal insulin levels across all groups and all animals had a significant increase in insulin secretion compared to basal levels. Note the blunted first phase response seen in 3-month-old KO mice and the augmented first and second phase response seen in 12-month-old KO mice.

Example 9

Intraislet Somatostatin

Preliminary data suggest the presence of delta-to-beta cell endocrine axis within the islet in which intraislet somatostatin inhibits insulin secretion. The purpose of this example is to prove the following hypotheses: 1) intraislet somatostatin inhibits insulin secretion via a delta-to-beta cell endocrine axis in the human, rat and mouse pancreas and that the effect is glucose-dependent; 2) the somatostatin receptor subtype responsible for the inhibition of insulin is species-specific; and 3) genetic ablation of the somatostatin receptor subtype 5 will alter insulin secretion and glucose homeostasis in the mouse.

The effect of intraislet somatostatin is determined by examining the insulin response to immunoneutralization of intraislet somatostatin with antibodies and FAb fragments of antibodies directed against somatostatin in isolated perfused human, rat and mouse pancreas models. Electron microscopy is used to help to determine the compartment of immunoneutralization. The somatostatin receptor subtype responsible for the inhibition of insulin is determined by examining the response of insulin secretion to infusions of specific somatostatin receptor subtype agonists in these models. Immunohistochemistry is performed using polyclonal antibodies directed against SSTR 1–5 to determine which receptor subtypes are present in the human, rat and mouse pancreas.

The somatostatin receptor subtype 5 appears responsible for the inhibition of mouse insulin secretion. Thus, two models are developed using state-of-the-art transgenic techniques: the first is a total somatostatin receptor subtype 5 gene ablation model and the second is a β-cell-specific somatostatin receptor subtype 5 gene ablation model. In vivo and in vitro physiology studies are performed in these mice to determine the effect of genetically.altering the delta-to-beta cell endocrine axis on insulin secretion and glucose homeostasis. The pancreas of the gene-ablated mice are studied using immunohistochemistry with antibodies directed against the somatostatin receptor subtypes to determine if the somatostatin receptor subtypes are altered in the islets of the gene ablated mice.

Other studies involve a β-cell specific BETA2 knockout mouse model and promoter analysis of the SSTR5 gene including the role of the transcription factor BETA2 in activation of the SSTR5 gene and insulin expression. The results will elucidate physiologic mechanisms regulating insulin secretion and determine whether there are species differences in this regulation. Furthermore, pathophysiologic consequences to genetically altering these mechanisms may be determined.

Other embodiments and uses of the invention will be apparent to those skilled in the art from consideration of the specification and practice of the invention disclosed herein. All references cited herein, including all U.S. and foreign patents and patent applications, are specifically and entirely incorporated by reference, including, but not limited to, U.S. Provisional Patent Application No. 60/161,109, filed Oct. 22, 1999, and entitled "Promoter Driven Tissue Specific Cytotoxic Agents" and U.S. Provisional Patent Application No. 60/224,382, filed Aug. 9, 2000, and entitled "Promoter Driven Tissue Specific Cytotoxic Agents and Methods of Use." It is intended that the specification and examples be considered exemplary only, with the true scope and spirit of the invention indicated by the following claims.

What is claimed is:

1. A method of treating pancreatic adenocarcinoma in a subject, comprising:
   a) directly administering to a subject a nucleic acid comprising a vector with an insulin promoter having SEQ ID No. 1 operatively coupled to a cytotoxic gene, wherein the cytotoxic gene is thereby expressed in a pancreatic adenocarcinoma cell,
   b) administering a pro-drug to said subject, wherein the prodrug is converted to a cytotoxic compound by the action of the protein encoded by said cytotoxic gene and thereby killing the pancreatic adenocarcinoma cell.

2. The method of claim 1, where the cytotoxic gene is the thymidine kinase gene.

3. The method of claim 1, where the cytotoxic gene is the thymidine kinase gene and the prodrug is acyclovir, ganciclovir, FIAU or 6-methoxypurine arabinoside.

* * * * *

UNITED STATES PATENT AND TRADEMARK OFFICE
CERTIFICATE OF CORRECTION

Figure 1B:
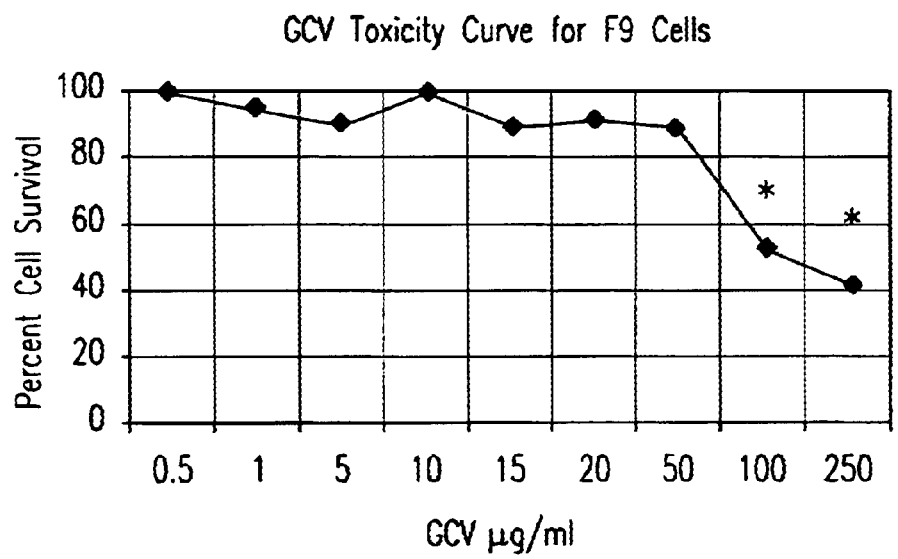
FIG. 1B is a dose response curve for F9 cells given GCV.

PATENT NO. : 6,716,824 B1
DATED : April 6, 2004
INVENTOR(S) : Charles F. Brunicardi It is certified that error appears in the above-identified patent and that said Letters Patent is hereby corrected as shown below:

Column 19,
Line 43, delete "FIG. 1 5B" and insert -- "FIG. 1B" --

Column 26,
Line 43, delete "will" and insert -- "well" --

Column 28,
Line 8, in the sequence listing, delete the lowercase "t" and insert an uppercase -- "T" --.

Signed and Sealed this

Seventeenth Day of August, 2004

JON W. DUDAS
*Acting Director of the United States Patent and Trademark Office*